ically feeds medicament to the needle or cannula (12, 62, 122), allowing for even smaller gauge needles for improved patient comfort.

United States Patent
Knapp et al.

(10) Patent No.: US 10,918,807 B2
(45) Date of Patent: Feb. 16, 2021

(54) DISPOSABLE PEN NEEDLE WITH ABBREVIATED NON-PATIENT END, AND REUSABLE PEN INTERFACE

(71) Applicant: Becton, Dickinson and Company, Franklin Lakes, NJ (US)

(72) Inventors: Keith Knapp, Warwick, NY (US); Sudarsan Srinivasan, North Brunswick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 478 days.

(21) Appl. No.: 15/578,546

(22) PCT Filed: May 31, 2016

(86) PCT No.: PCT/US2016/035104
§ 371 (c)(1),
(2) Date: Nov. 30, 2017

(87) PCT Pub. No.: WO2016/196518
PCT Pub. Date: Dec. 8, 2016

(65) Prior Publication Data
US 2018/0169350 A1 Jun. 21, 2018

Related U.S. Application Data

(60) Provisional application No. 62/169,408, filed on Jun. 1, 2015.

(51) Int. Cl.
*A61M 5/32* (2006.01)
*A61M 5/34* (2006.01)
*A61M 5/24* (2006.01)

(52) U.S. Cl.
CPC ........ *A61M 5/3286* (2013.01); *A61M 5/3293* (2013.01); *A61M 5/345* (2013.01);
(Continued)

(58) Field of Classification Search
CPC .. A61M 5/3293; A61M 5/3286; A61M 5/345; A61M 5/34; A61M 5/347; A61M 5/3202; A61M 5/321; A61M 5/343
See application file for complete search history.

(56) References Cited

U.S. PATENT DOCUMENTS 1,746,009 A 2/1930 Mulford
3,092,108 A 6/1963 Friedman
(Continued)

FOREIGN PATENT DOCUMENTS

DE 102008025002 A1 12/2009
EP 2703028 A1 3/2014
(Continued)

*Primary Examiner* — Jason E Flick
*Assistant Examiner* — Tasnim Mehjabin Ahmed
(74) *Attorney, Agent, or Firm* — Dickinson Wright PLLC

(57) ABSTRACT

A medicament delivery system is disclosed including disposable pen needles (10, 60, 120) each having a stainless steel needle or cannula (12, 62, 122) with a concealed or a very short non-injection end (28, 78, 128) that is not intended to pierce the septum (8) of the drug storage compartment (6) of a medication pen (2), thus reducing the risk of needle stick injuries. Several types of non-metallic interfaces (30, 80, 100) serve as intermediaries between the pen needles (10, 60, 120) and a medication pen (2) and perform the septum-piercing function. These improve the flow of medicament to the needle or cannula (12, 62, 122) due to the larger lumen of the plastic interface (30, 80, 100) that directly feeds medicament to the needle or cannula (12, 62, 122), allowing for even smaller gauge needles for improved patient comfort.

11 Claims, 22 Drawing Sheets

(52) U.S. Cl.
CPC ........... *A61M 5/347* (2013.01); *A61M 5/2466* (2013.01); *A61M 5/321* (2013.01); *A61M 5/3202* (2013.01)

(56) References Cited

U.S. PATENT DOCUMENTS

| | | | |
|---|---|---|---|
| 2004/0254543 A1* | 12/2004 | Griffiths | A61M 5/2066 604/263 |
| 2009/0018503 A1 | 1/2009 | Walton et al. | |
| 2009/0247958 A1 | 10/2009 | Carlyon | |
| 2010/0286610 A1 | 11/2010 | Chang | |
| 2010/0292656 A1* | 11/2010 | Groskopf | A61M 5/3134 604/200 |
| 2011/0152822 A1* | 6/2011 | Drunk | A61M 5/329 604/415 |
| 2011/0230827 A1* | 9/2011 | Mori | A61M 5/2448 604/82 |
| 2012/0150128 A1 | 6/2012 | Zhao | |
| 2015/0126925 A1 | 5/2015 | Fuke et al. | |
| 2015/0328412 A1 | 11/2015 | Bates et al. | |

FOREIGN PATENT DOCUMENTS

| | | |
|---|---|---|
| JP | 2014528783 A | 10/2014 |
| TW | 200948408 A1 | 12/2009 |
| WO | WO-2012043161 | 4/2012 |
| WO | WO-2014105667 A2 | 7/2014 |
| WO | WO-2017189169 A1 | 11/2017 |
| WO | WO-2017189171 A1 | 11/2017 |

\* cited by examiner

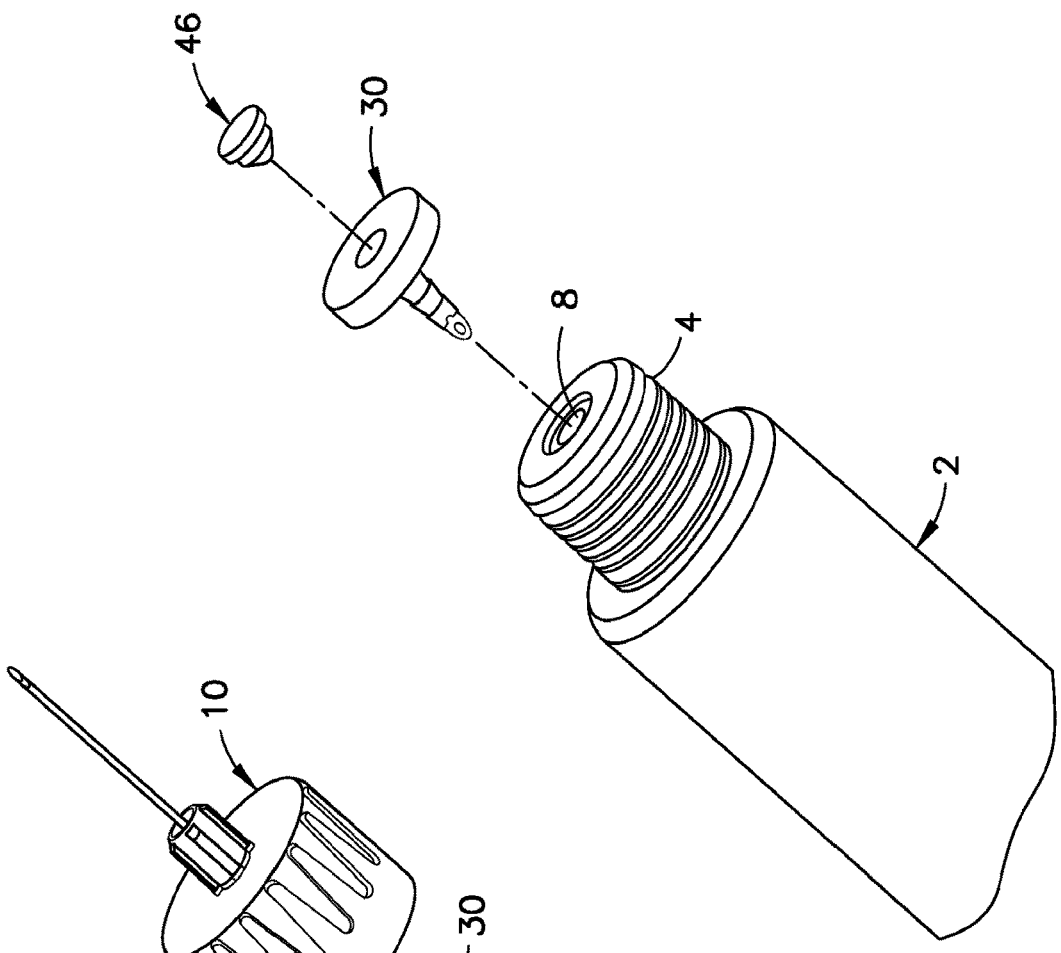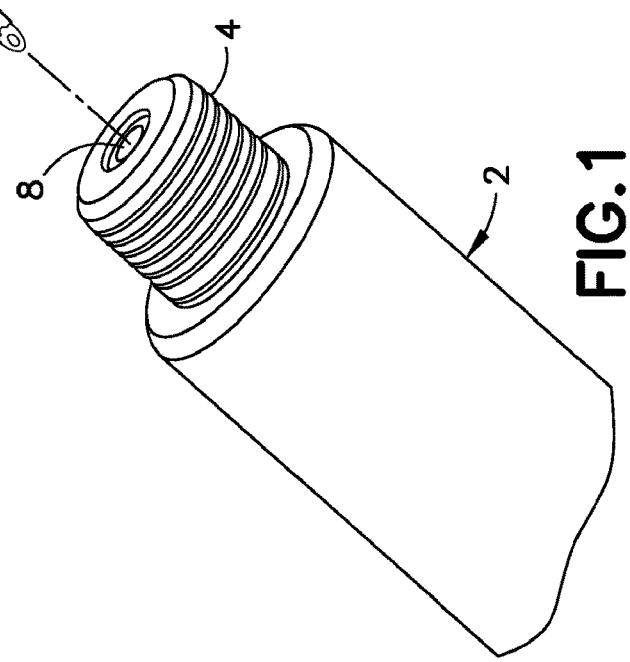

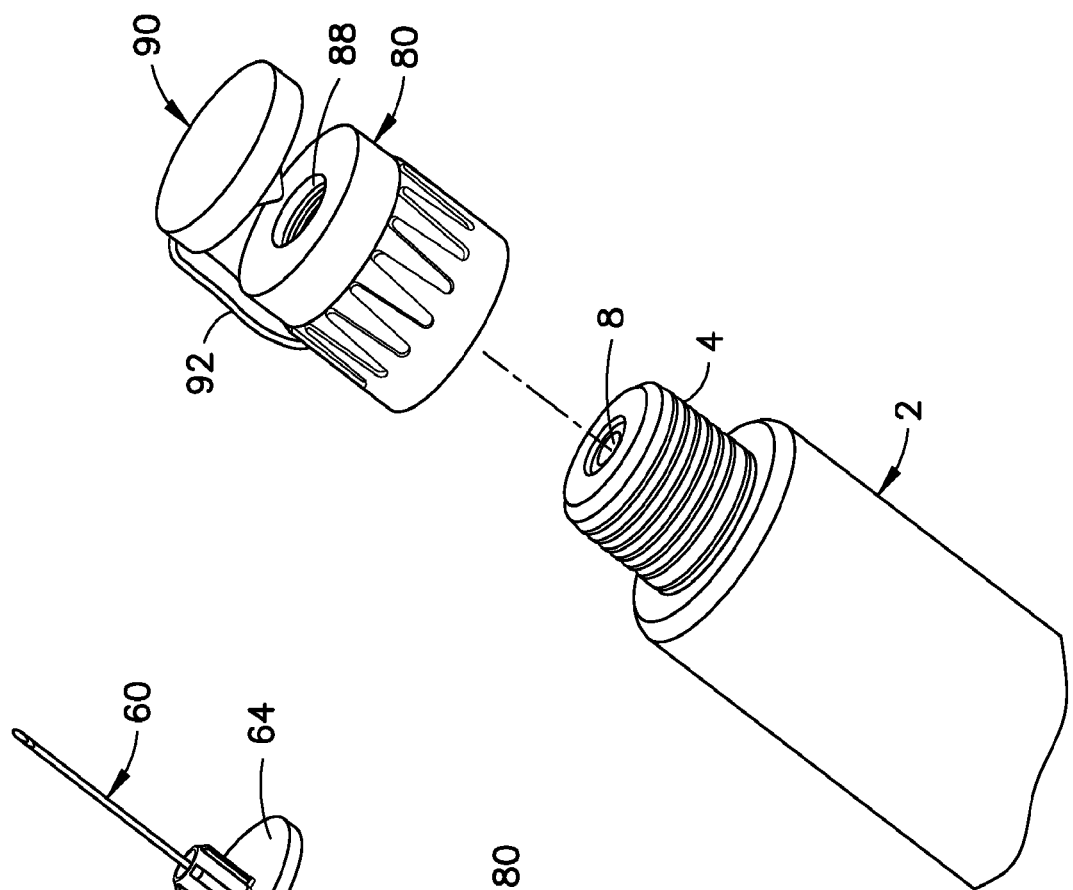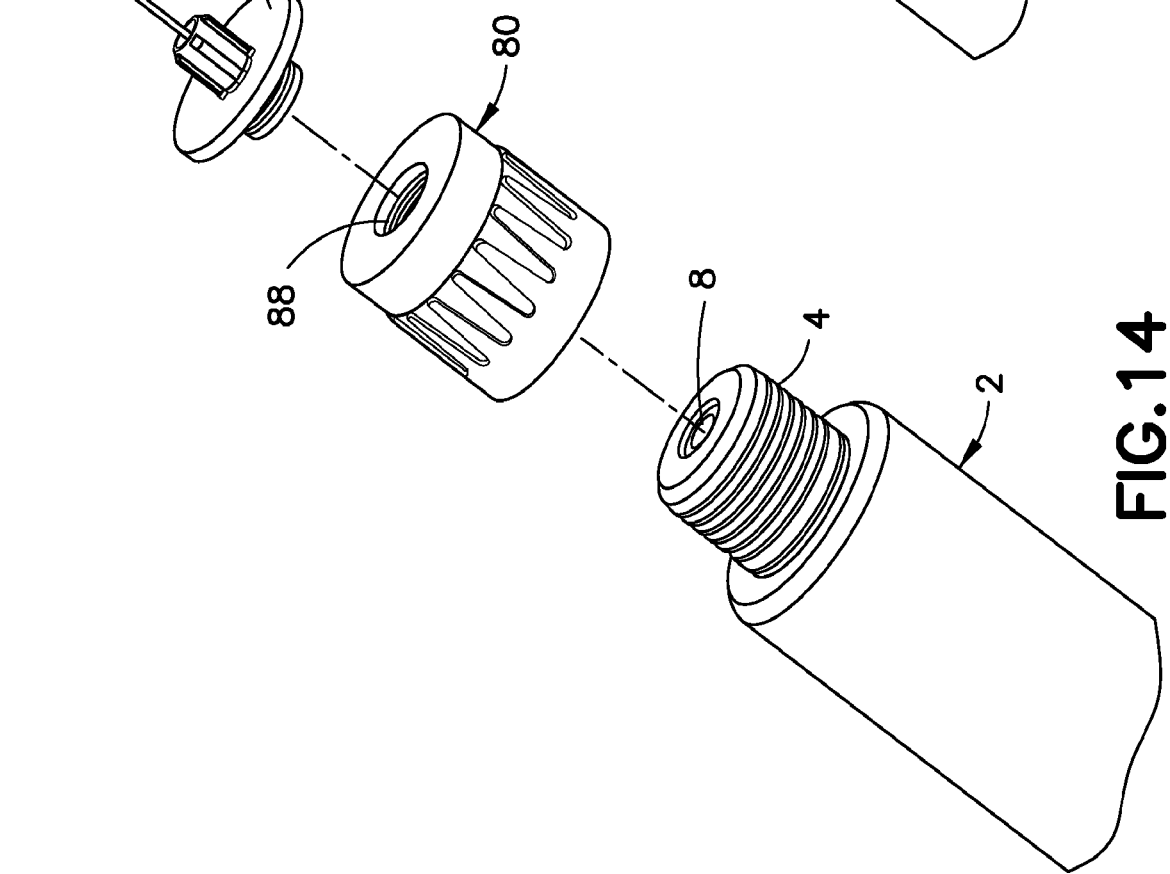

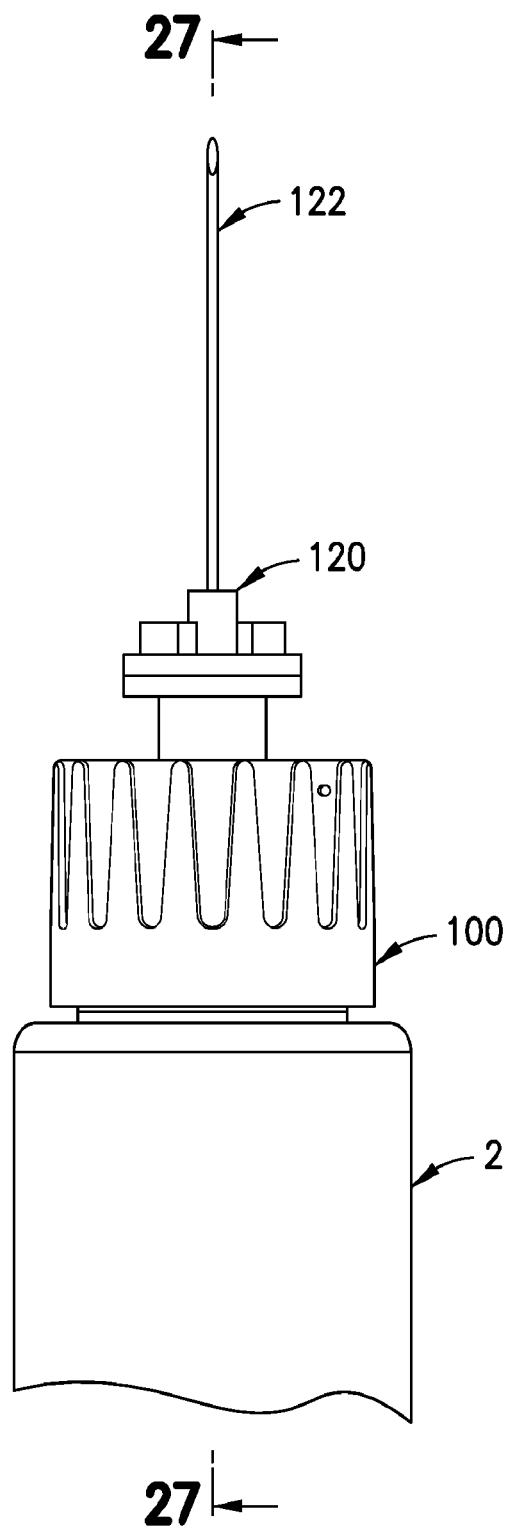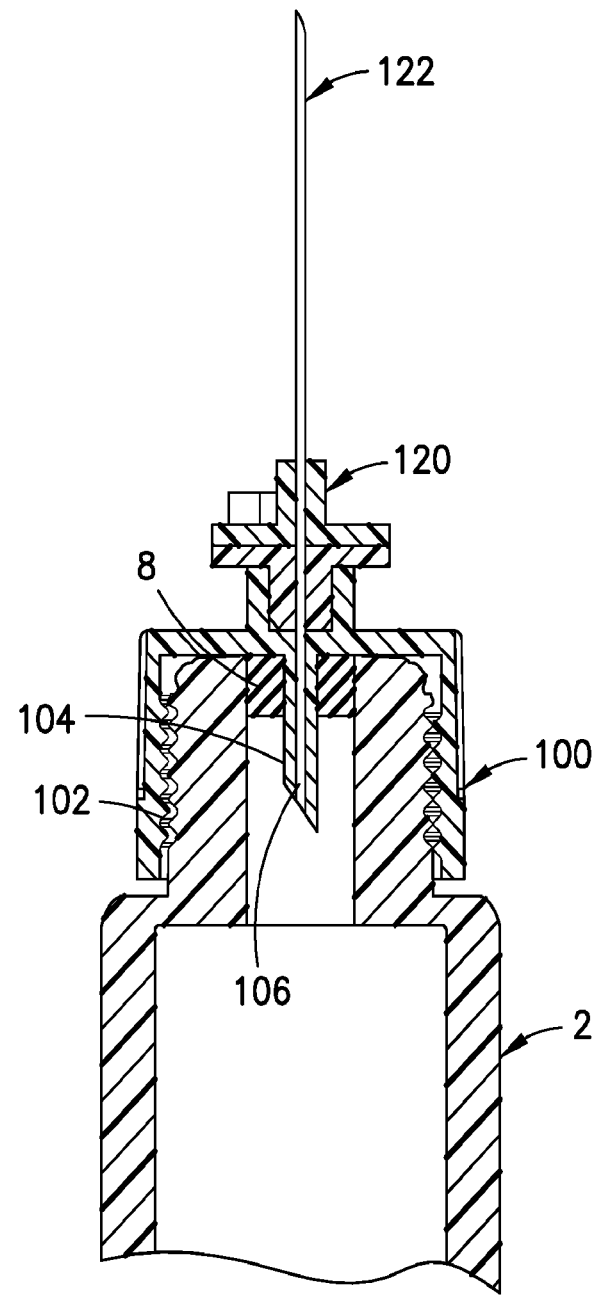
FIG.26
FIG.27

DISPOSABLE PEN NEEDLE WITH ABBREVIATED NON-PATIENT END, AND REUSABLE PEN INTERFACE

RELATED APPLICATIONS

This application is the U.S. national stage of International Application No. PCT/US16/35104, filed on May 31, 2016, which claims priority to U.S. Provisional Application No. 62/169,408, filed on Jun. 1, 2015.

BACKGROUND OF THE INVENTION

1. Field of the Invention

The invention is directed to a disposable pen needle for use with a drug delivery device, such as a medication pen, and an interface for removably joining the pen needle and the drug delivery device.

2. Description of Related Art

Pen needles are widely used in medication delivery systems for self-administered injectable drugs. Commonly used pen needles have a single stainless steel cannula (hollow needle) extending through a needle-bearing hub. The non-patient (non-injection) end of the needle pierces the septum of the drug storage compartment of the medication pen, while the patient (injection) end of the needle is adapted for insertion into the patient's tissue.

Such pen needles typically have a uniform gauge, so both ends of the cannula have the same inner and outer diameters. Thinner needles (generally greater than 28 gauge) may be preferred for patient comfort, but if these are of uniform gauge they may not reliably pierce the conventionally thick septum of the drug storage compartment, e.g., due to needle buckling, and/or may unduly restrict flow. Solutions to these problems have included needles with a thicker non-injection end; however, such dual-gauge needles tend to be difficult and costly to manufacture.

Standard pen needles, if mishandled, can also present a risk of needle stick injury at the non-patient end during assembly with and removal from the medication pen, and during used pen needle disposal. Protective solutions typically have entailed the use of rather elaborate shielding arrangements for the non-patient end. See, for example, U.S. Pat. Nos. 7,314,464, 7,384,414 and 7,462,168, all of which are assigned to the assignee of the present application, and the disclosures of which are fully incorporated herein by reference.

SUMMARY OF THE INVENTION

The invention affords simple and effective solutions to the above-noted problems by providing several types of disposable (i.e., single-use) pen needles, each having an abbreviated non-injection (non-patient) end, i.e., one that is not intended to pierce the septum of the drug storage compartment of a medication pen. Several types of interfaces are provided to serve as intermediaries between these pen needles and a medication pen. The interfaces are equipped to pierce the septum of the pen's drug storage compartment and thereby enable drug flow to a mounted pen needle.

In one aspect, the invention concerns a disposable pen needle that includes a hub having a distal hub portion, a proximal hub portion adapted for attachment to a medicament delivery device, and a hub bore extending through the hub from the distal hub portion to the proximal hub portion. A needle (cannula) is mounted to the hub, the needle having a distal injection end and a proximal needle portion terminating in a non-injection end. At least part of the proximal needle portion resides in the hub bore, and the non-injection end of the needle, if exposed outside the hub bore, is spaced from the hub no more than about one-half the length of the hub bore. Thus, in some embodiments the non-injection end of the needle is not exposed outside the hub bore and need not be beveled or sharpened, while in other embodiments the non-injection end is exposed outside the hub bore for example, to pierce a relatively thin septum of a certain type of interface but not enough to be vulnerable to bending or to present a significant risk of needle stick injury.

In embodiments according to this aspect of the invention, the proximal hub portion includes internal threads adapted to mount the pen needle. In other embodiments, the proximal hub portion includes external threads adapted to mount the pen needle. In still other embodiments, the proximal hub portion includes a mounting boss through which the hub bore extends. In certain embodiments, the distal hub portion and the proximal hub portion are separately formed parts, each having a respective hub bore segment, and the hub portions are joined together with their hub bore segments aligned after the needle is mounted in the hub bore segment of the distal hub portion.

In another aspect, the invention concerns a reusable interface adapted for use between a medicament delivery device and a disposable pen needle. The interface includes a body having a spike adapted to pierce a seal (septum) of a medicament container housed in the device, and a recess axially aligned with the spike and adapted to mate with a disposable pen needle. The spike has an axial bore that extends through the spike and communicates with the recess. "Reusable" in the context of the invention means an interface that can be left installed on a medicament delivery device and used with a succession of disposable pen needles.

In embodiments according to this aspect of the invention, the body has a collar that surrounds the spike and is adapted to mate with a portion of the device. In these and other embodiments, the collar may be internally threaded and/or the recess may be internally threaded or smooth. In other embodiments, there is a bore-sealing, puncturable septum in the recess. In any of these embodiments, the spike may be tapered and may have at least one transverse external rib. Any of these embodiments may include a cap adapted to cover the recess when the interface is not mated with a pen needle; and the cap may be tethered to the body or separate from it.

Yet another aspect of the invention concerns a medicament delivery system that includes any of the disposable pen needle embodiments disclosed herein combined with any of the reusable interfaces disclosed herein.

BRIEF DESCRIPTION OF THE DRAWING FIGURES

Embodiments of the disclosed invention are described in detail below only by way of example, with reference to the accompanying drawings, in which:

FIG. 1 is an exploded perspective view of a first embodiment of a pen needle and a mating interface according to the invention adjacent a conventional medication pen to which they can be attached;

FIG. 2 is an exploded perspective view similar to FIG. 1 showing a sealing cap in lieu of the pen needle of FIG. 1;

FIG. 14 is an exploded perspective view of a second embodiment of pen needle and mating interface according to the invention adjacent a conventional medication pen to which they can be attached;

FIG. 15 is an exploded perspective view similar to FIG. 14 showing a sealing cap in lieu of the pen needle of FIG. 14;

FIG. 26 is an elevational view of the components of FIGS. 24 and 25 assembled with a conventional medication pen;

FIG. 27 is a cross-sectional view thereof taken along line 27-27 in FIG. 26;

Figure 3:
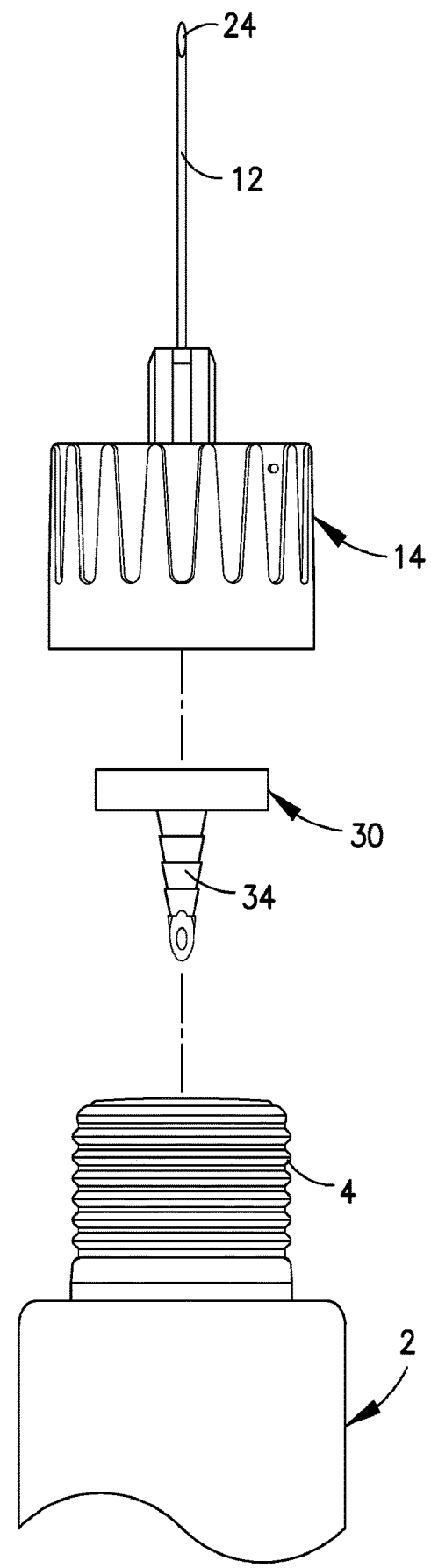
FIG. 3 is an exploded elevational view of the components shown in FIG. 1.

The figures are generally schematic and not necessarily to scale.

DETAILED DESCRIPTION OF THE PREFERRED EMBODIMENTS

As used herein, the "distal" direction is the direction toward the injection site, i.e., toward the patient (injection) end of the needle (cannula), and the "proximal" direction is the opposite direction, i.e., toward the non-patient (non-injection) end of the needle. The "axial" direction is along, or parallel to, the longitudinal axis of the needle, which is generally arranged axially on a medication pen.

A conventional medication pen 2 shown in many of the drawing figures has an externally threaded end 4 for mounting a pen needle and houses a medicament container 6 having a pierceable septum 8 at its dispensing end.

Figure 6:
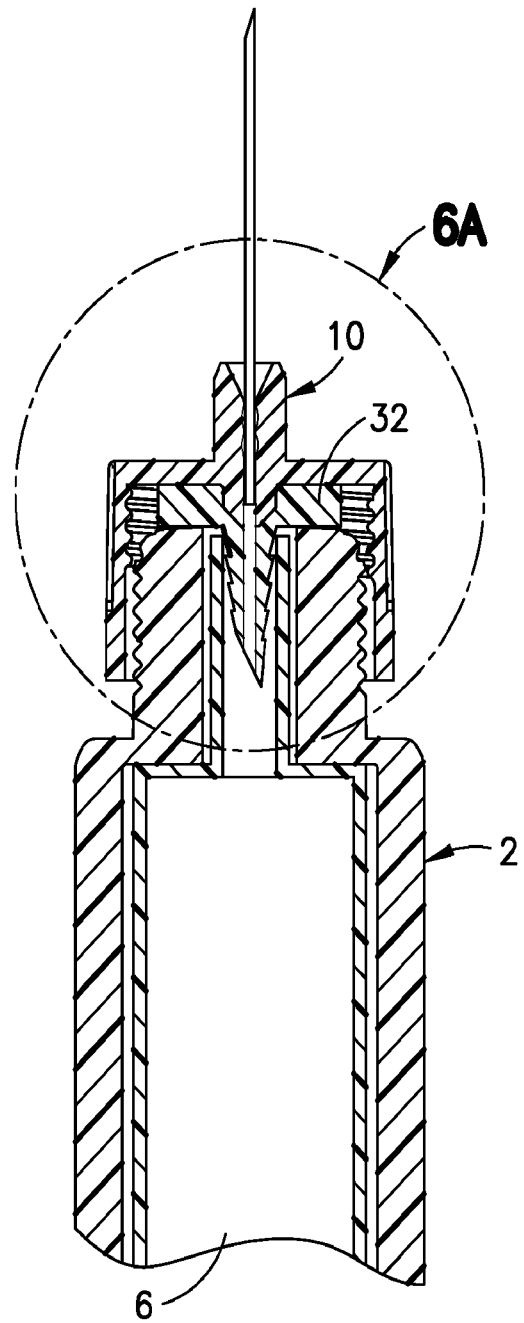
FIG. 6 is a cross-sectional view thereof taken along line 6-6 in FIG. 5.
Figure 6A:
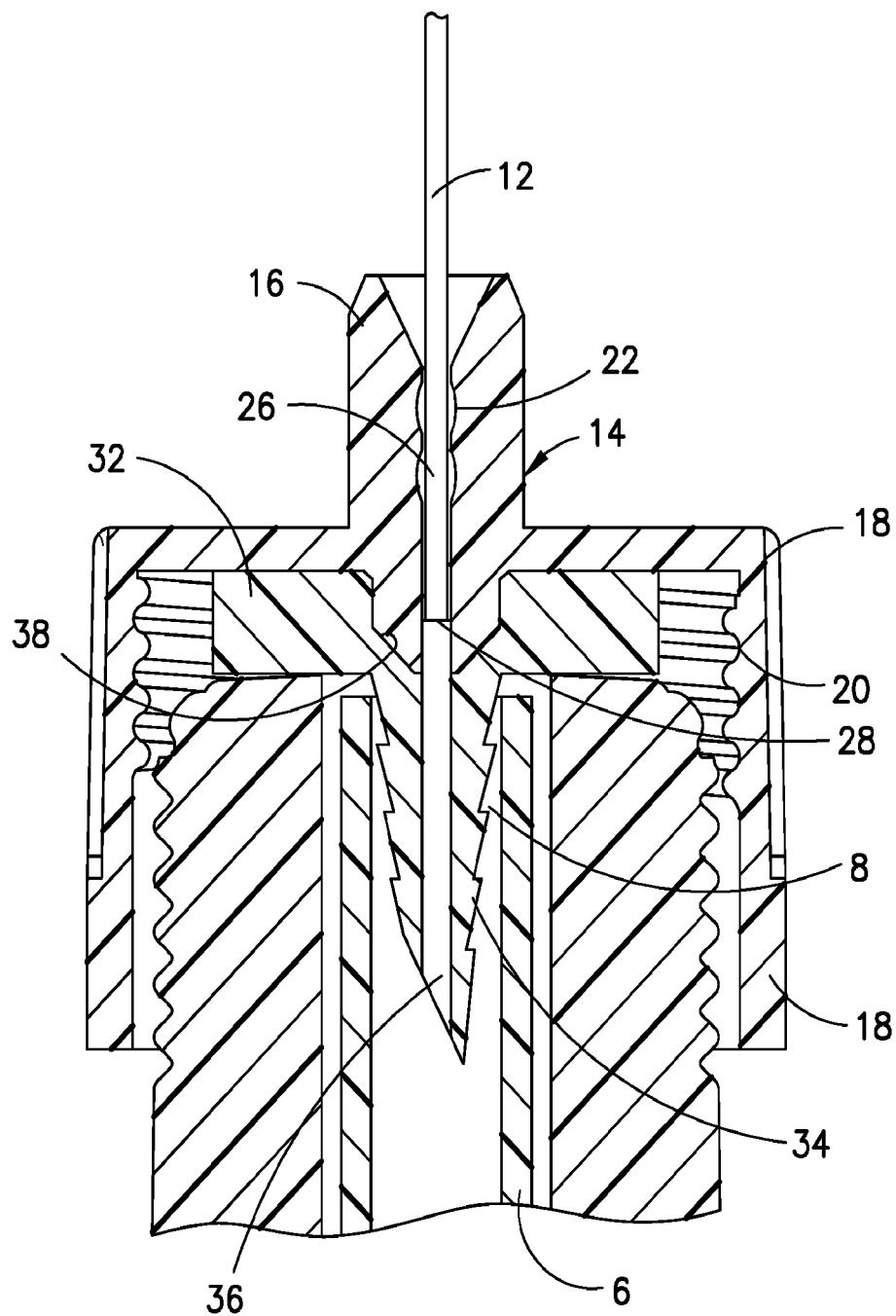
FIG. 6A is an enlarged detail view thereof taken along line 6A-6A in FIG. 6.
Figure 7:
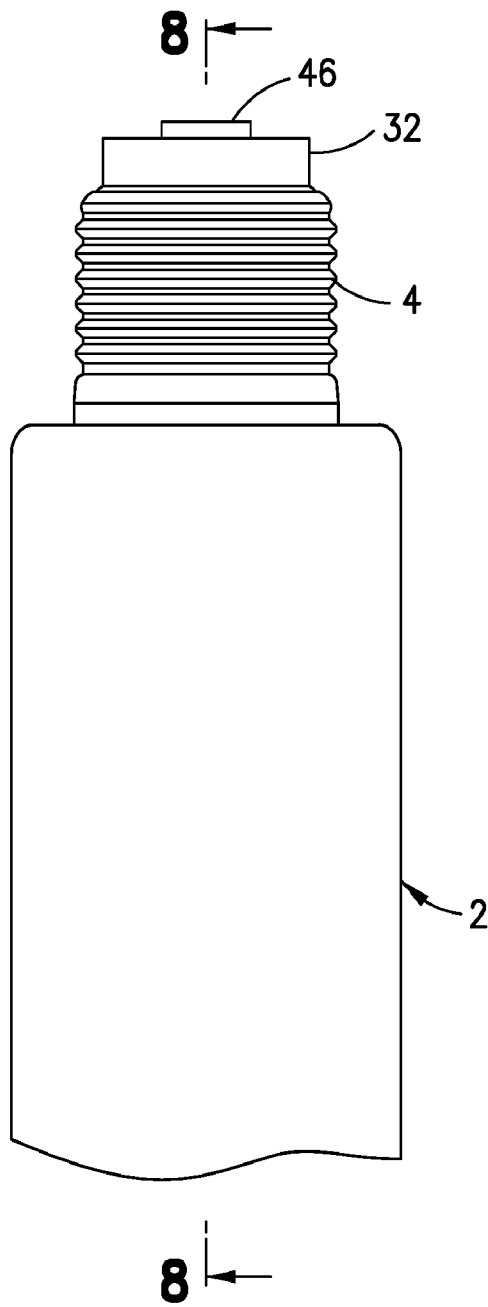
FIG. 7 is an elevational view of the assembled components shown in FIGS. 2 and 4.

Referring to FIGS. 1, 3, 5, 6 and 6A, a first embodiment of medicament delivery system according to the invention includes a disposable pen needle 10 and a reusable interface member 30. Pen needle 10 has a hollow stainless steel needle (cannula) 12 fixed to a hub 14, which preferably is made of a suitable plastic known in the art. As seen in FIG. 6A, hub 14 has a distal hub portion 16, a proximal hub portion (collar) 18 with internal threads 20 adapted to mate with the externally threaded end 4 of a medication pen 2, and an axially extending hub bore 22 open at both ends. Needle 12 has a beveled and sharpened distal injection end 24 and a proximal needle portion 26 with a non-injection end 28. Proximal needle portion 26 is fixed in hub bore 22 with an adhesive, such as epoxy or a UV-curable adhesive, by spin welding, by insert molding, or by other means known in the art.

Importantly, in this embodiment the non-injection end 28 of the needle is not beveled or sharpened, and is not exposed outside hub bore 22, so it cannot pierce septum 8 of container 6. Septum piercing is accomplished instead by interface member 30, which has a disk-like collar 32 from which a tapered spike 34 extends. Referring to FIG. 6A, the body of member 30 has an axial bore 36 open at both ends and a recess 38 in collar 32 axially aligned with the spike and open to bore 36. Distally raked ribs 40 on the outer surface of spike 34 serve to keep the spike from dislodging from the septum 8 of container 6.

Figure 8:
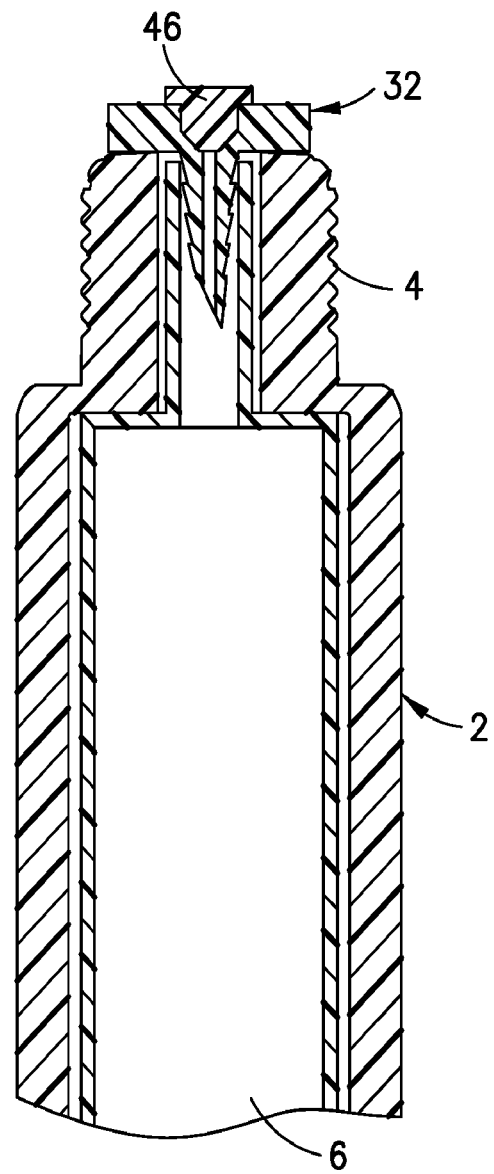
FIG. 8 is a cross-sectional view thereof taken along line 8-8 in FIG. 7.
Figure 8A:
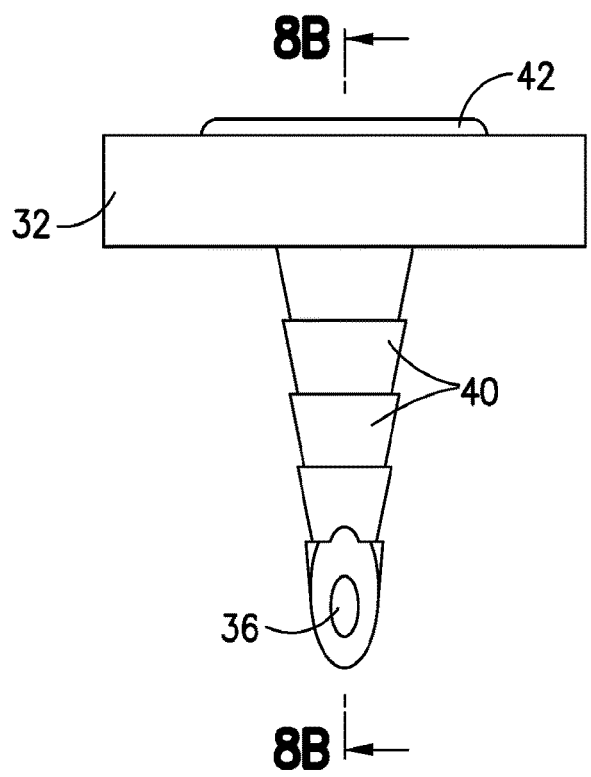
FIG. 8A is an enlarged elevational view of the interface member used in this embodiment.
Figure 8B:
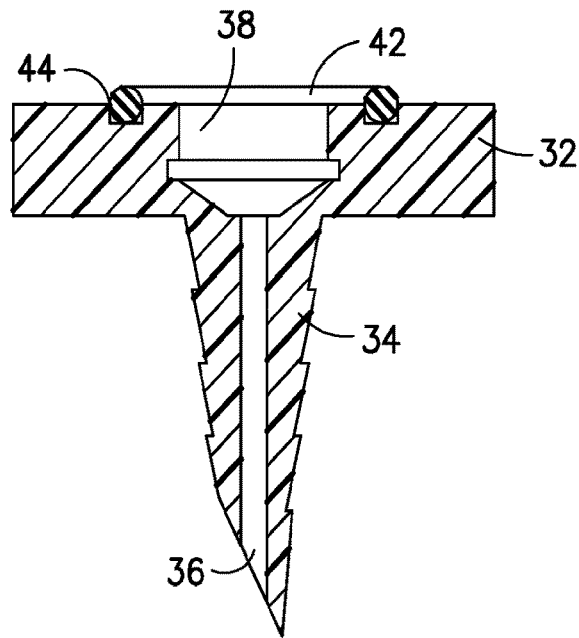
FIG. 8B is a cross-sectional view thereof taken along line 8B-8B in FIG. 8A.
Figure 8C:
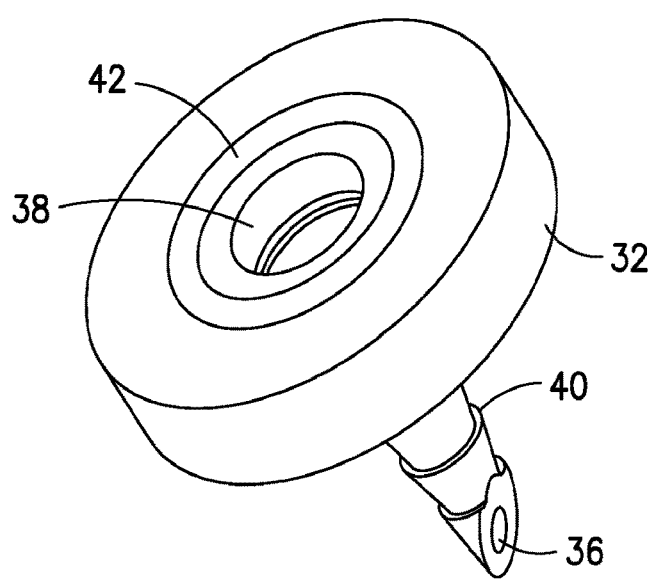
FIG. 8C is a perspective view thereof.
Figure 9:
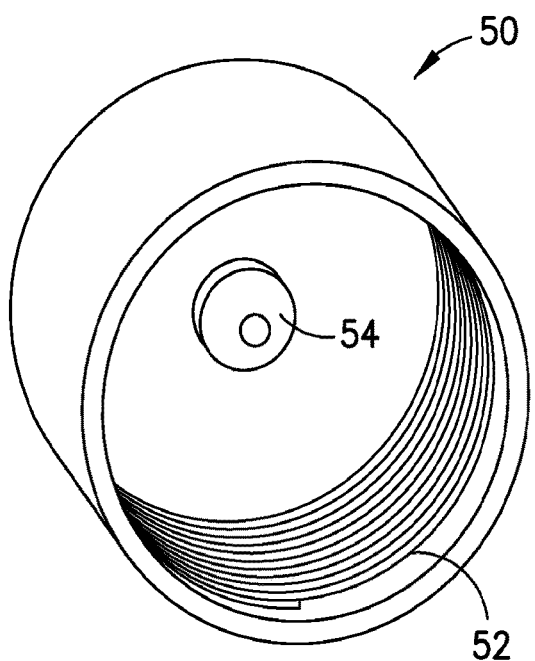
FIG. 9 is a perspective view of another sealing cap embodiment for use with the interface shown in the preceding figures.
Figure 10:
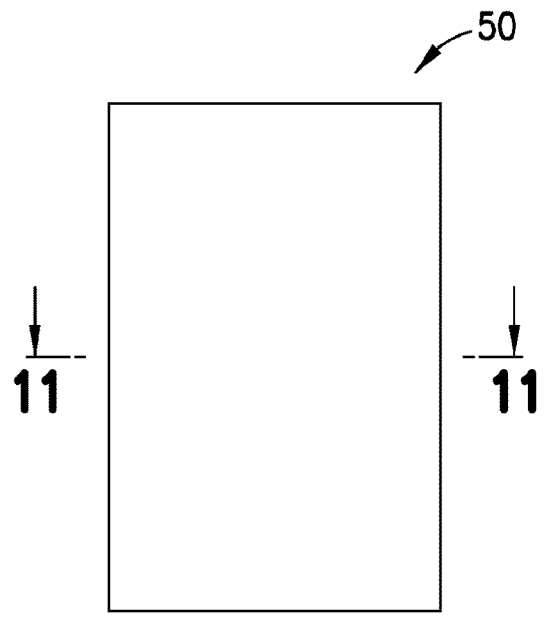
FIG. 10 is a side elevational view thereof.
Figure 11:
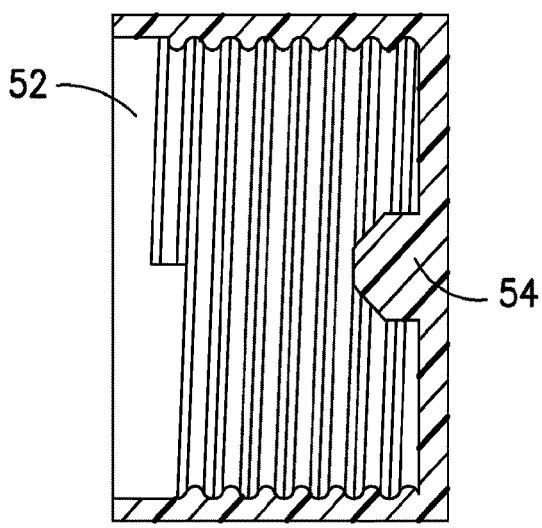
FIG. 11 is a cross-sectional view thereof taken along line 11-11 in FIG. 10.
Figures 12, 13:
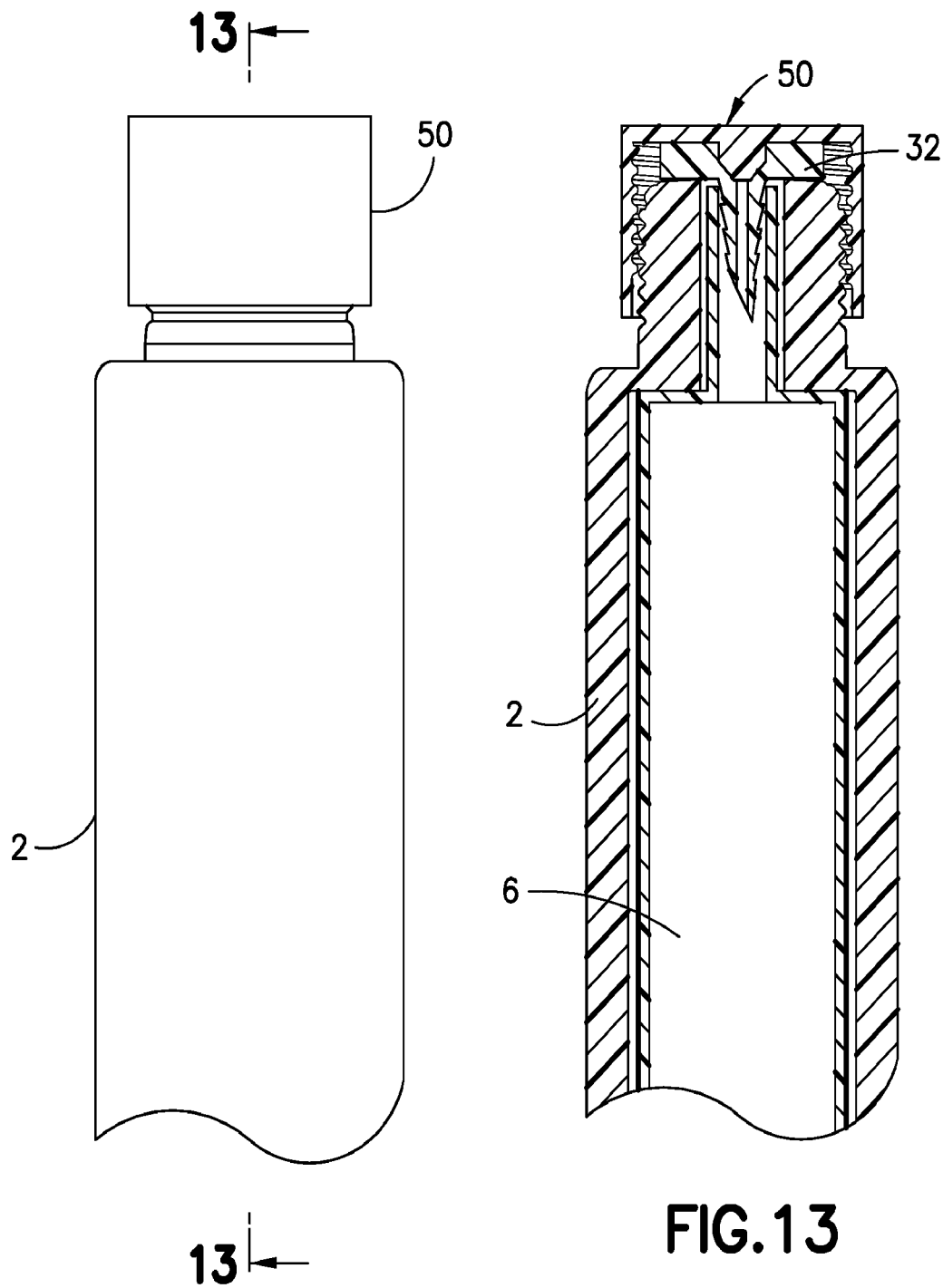
FIG. 12 is an elevational view of the sealing cap of FIGS. 9-11 covering the end of the medication pen.
FIG. 13 is a cross-sectional view thereof taken along line 13-13 in FIG. 12.

FIGS. 8A, 8B and 8C show an optional addition to interface member 30, specifically, an annular seal (O-ring) 42 seated in an annular groove 44 in the distal face of collar 32. This addition serves to enhance sealing with the hub 14 of a pen needle when installed on the medication pen, or with a cap when a pen needle is not installed.

Figure 4A:
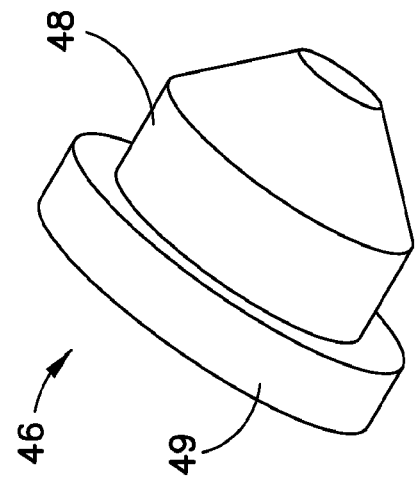
FIG. 4A is a perspective view of the sealing cap shown in FIGS. 2 and 4.
Figure 4:
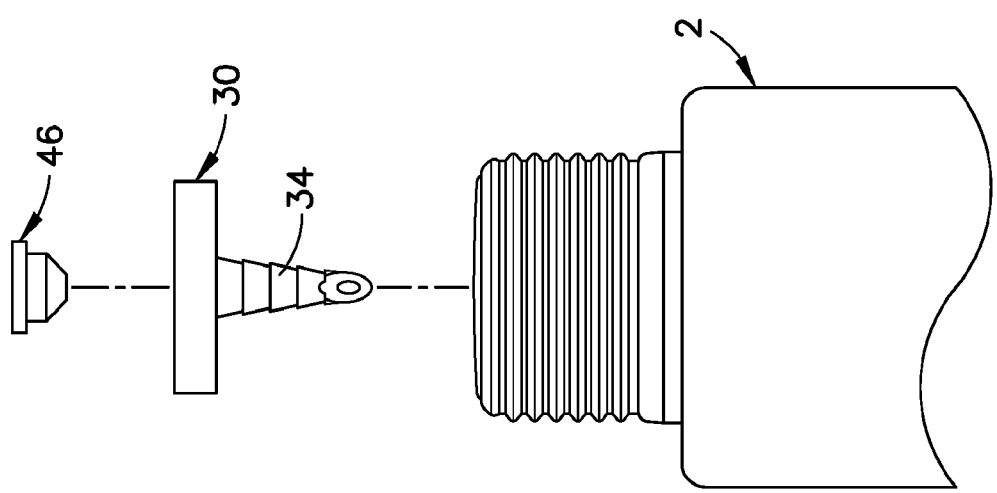
FIG. 4 is an exploded elevational view of the components shown in FIG. 2.
Figure 5:
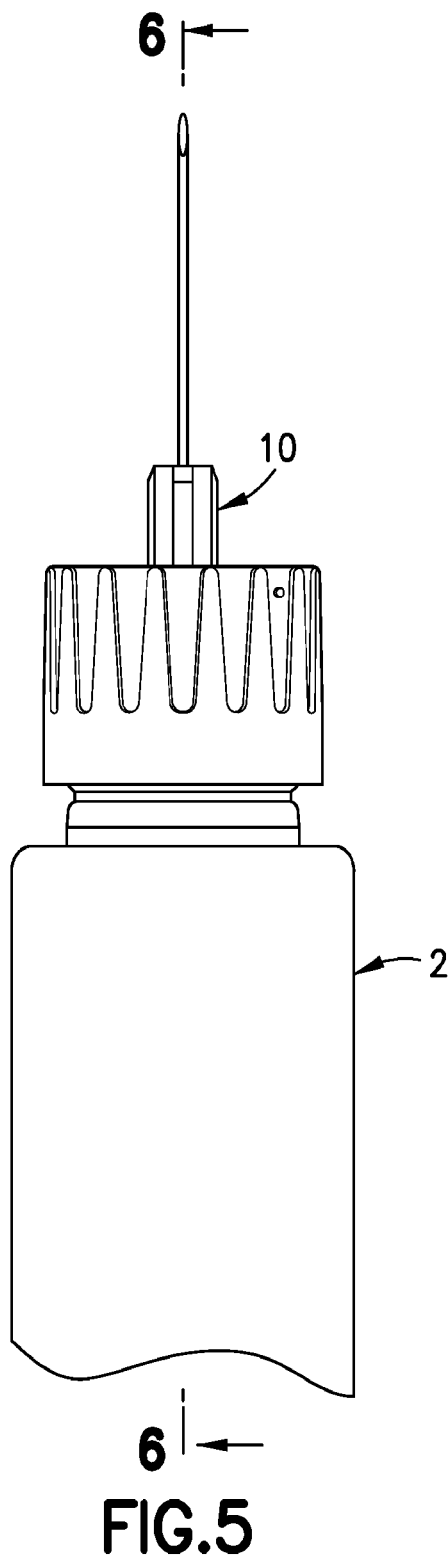
FIG. 5 is an elevational view of the assembled components shown in FIGS. 1 and 3.

FIG. 4A shows one type of cap 46 for sealing recess 38 in collar 32 when no pen needle is installed. Press-on cap 46, which is made of plastic or a resilient material such as silicone rubber, has a plug-like end 48 sized and shaped to fit snugly into recess 38, and an opposite flanged end 49 that enables the cap to be gripped and removed.

FIGS. 9-13 show another type of cap for sealing recess 38 in collar 32. This cap 50 preferably is made of plastic and is similar to hub 14 in that it has an internally threaded collar 52 adapted to mate with the externally threaded end 4 of a medication pen 2. However, the end of this cap is closed and it has in internal axial projection 54 sized and shaped like a plug to fit snugly into recess 38 in collar 32.

Figures 16, 17:
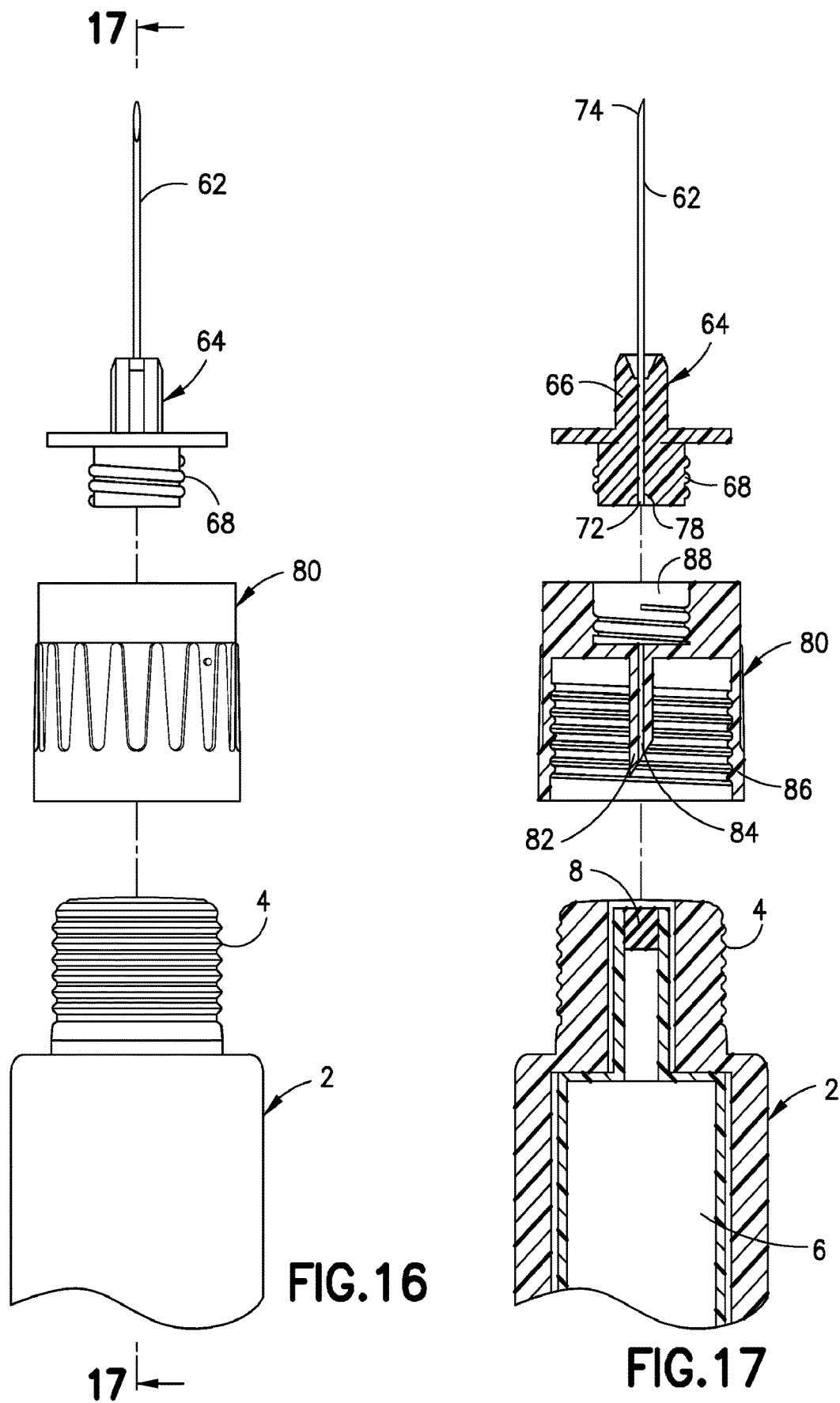
FIG. 16 is an exploded elevational view of the components shown in FIG. 15.
FIG. 17 is a cross-sectional view thereof taken along line 17-17 in FIG. 16.
Figure 18:
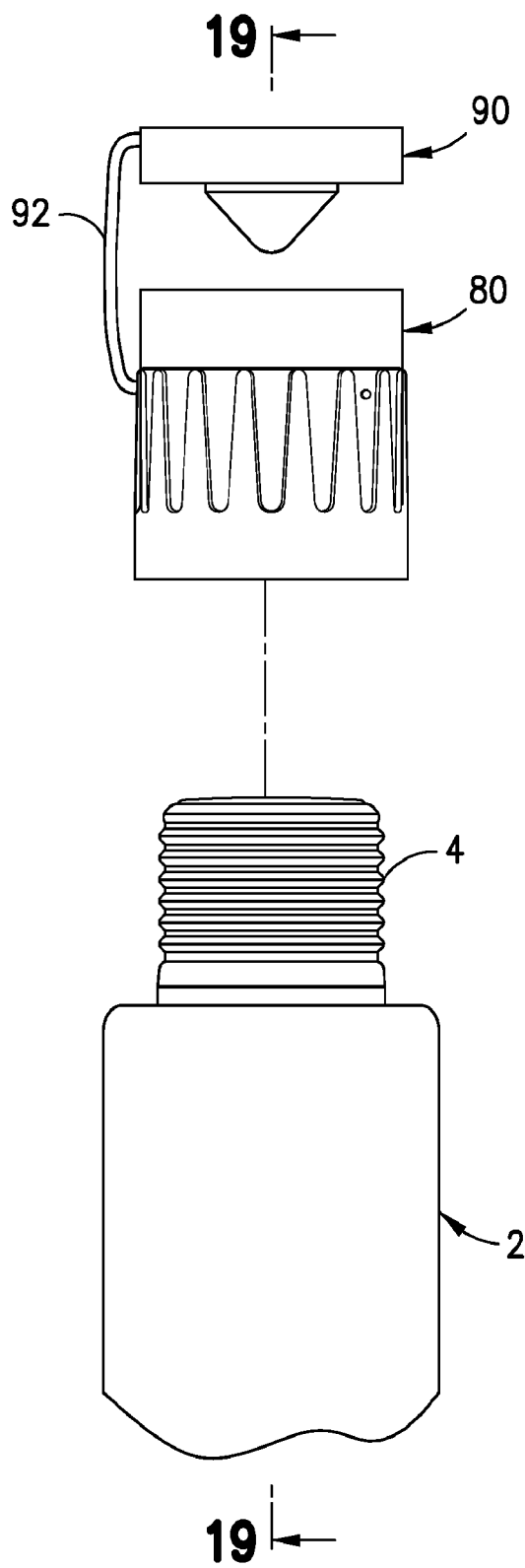
FIG. 18 is an exploded elevational view of the components shown in FIG. 15.
Figure 19:
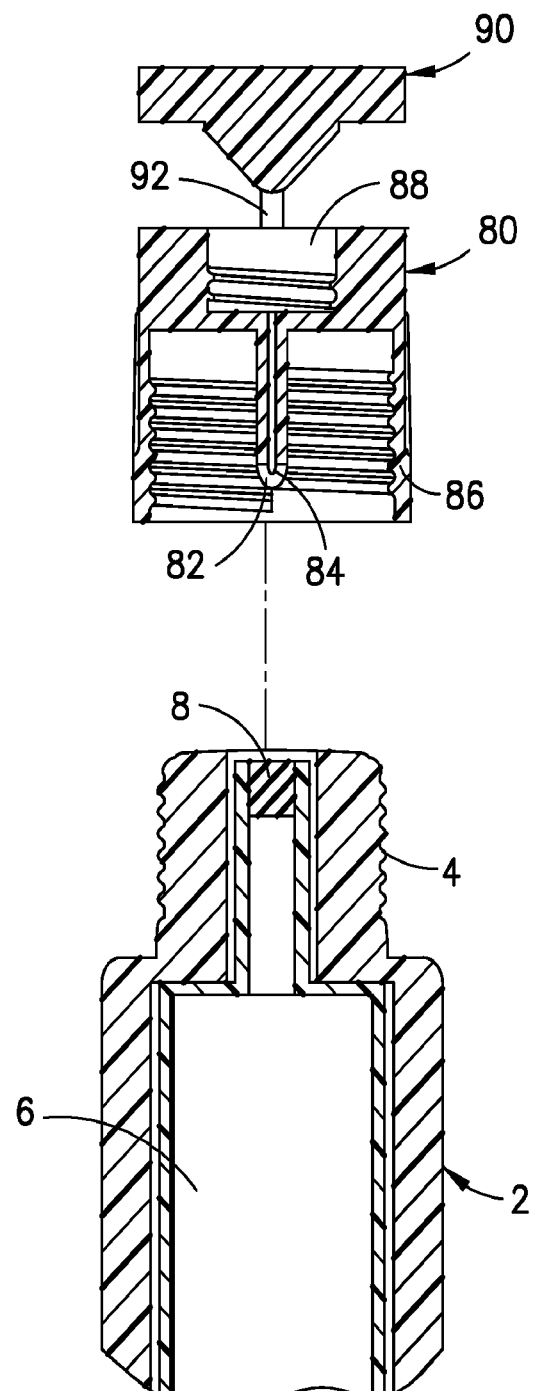
FIG. 19 is a cross-sectional view thereof taken along line 19-19 in FIG. 18.
Figure 20:
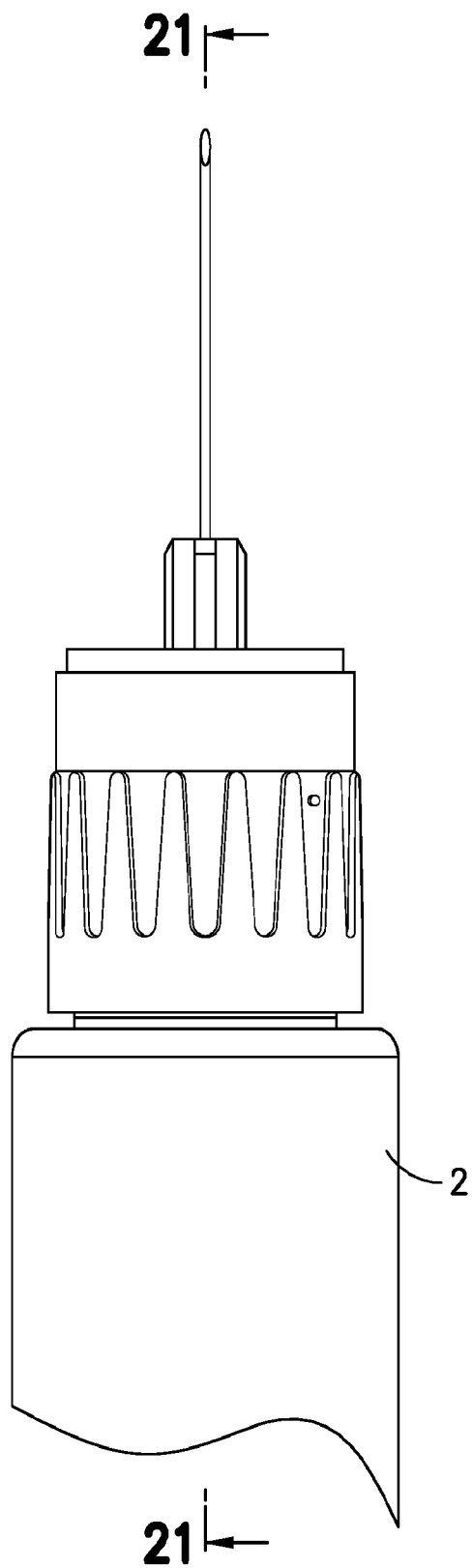
FIG. 20 is an elevational view of the assembled components shown in FIGS. 14 and 16.
Figure 21:
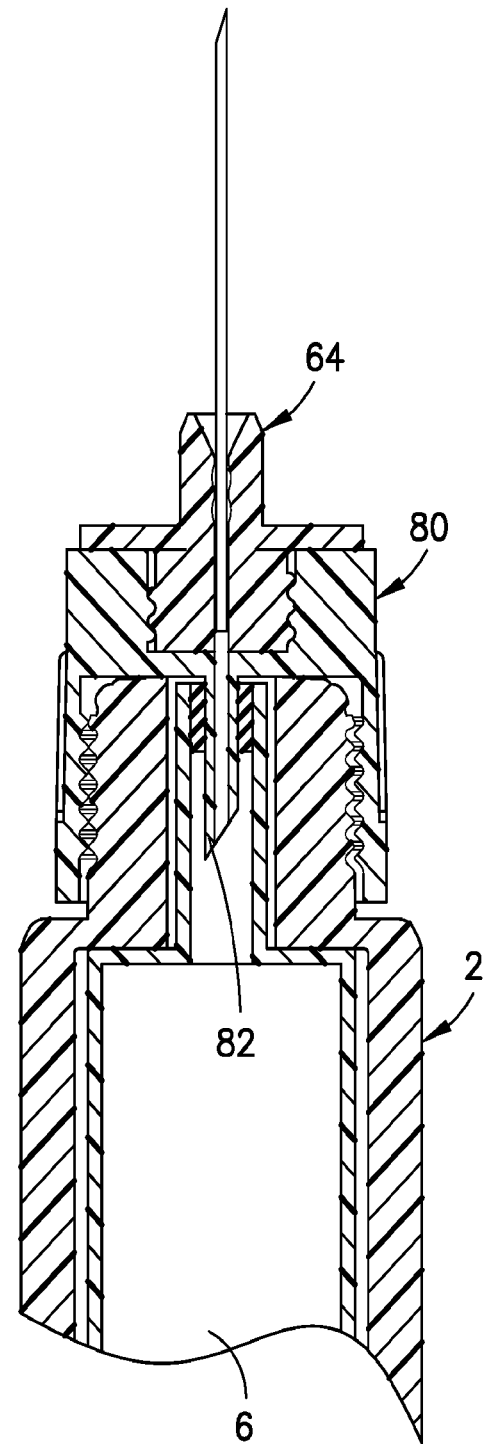
FIG. 21 is a cross-sectional view thereof taken along line 21-21 in FIG. 20.
Figure 22:
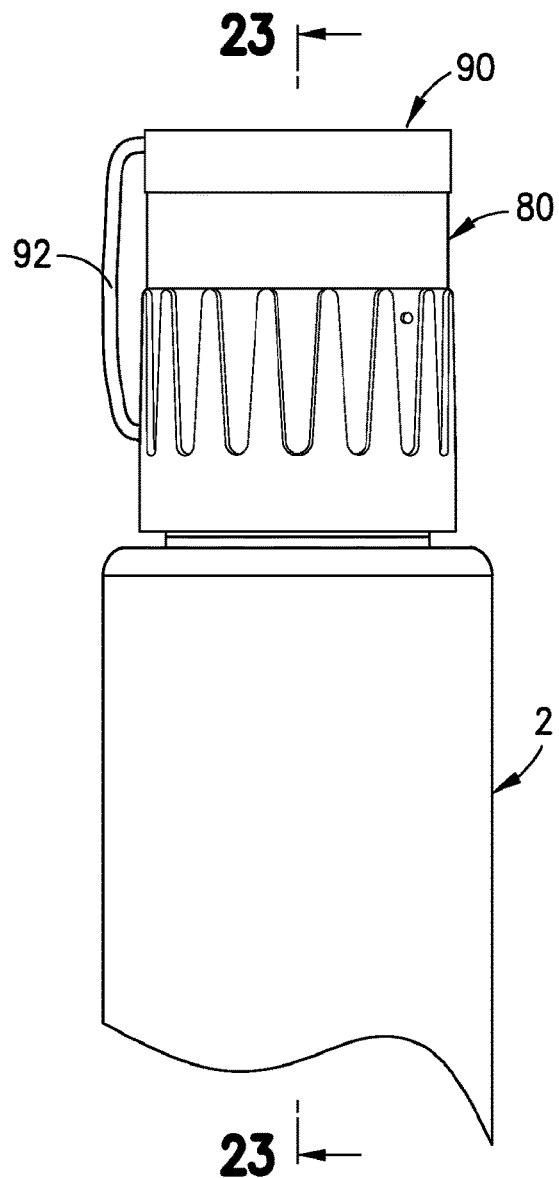
FIG. 22 is an elevational view of the assembled components shown in FIGS. 15 and 18.
Figure 23:
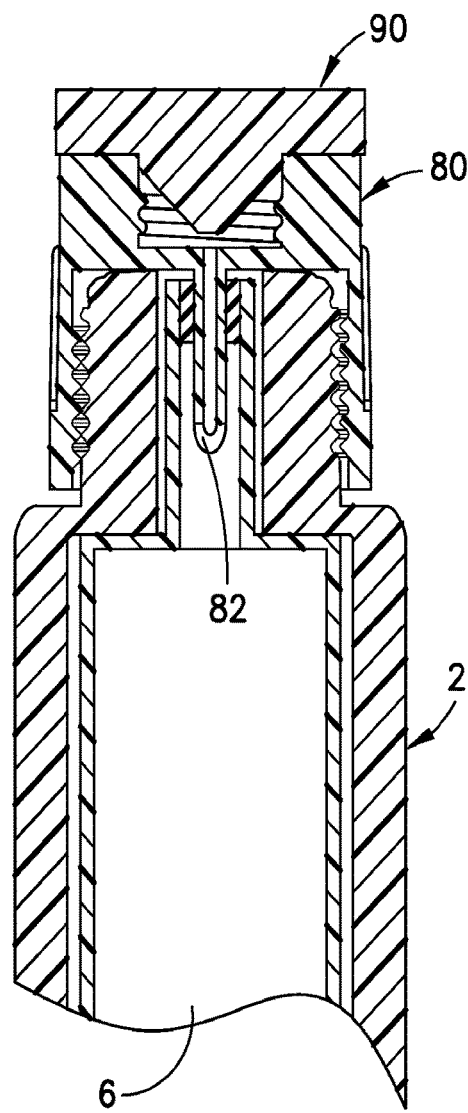
FIG. 23 is a cross-sectional view thereof taken along line 23-23 in FIG. 22.
Figure 24:
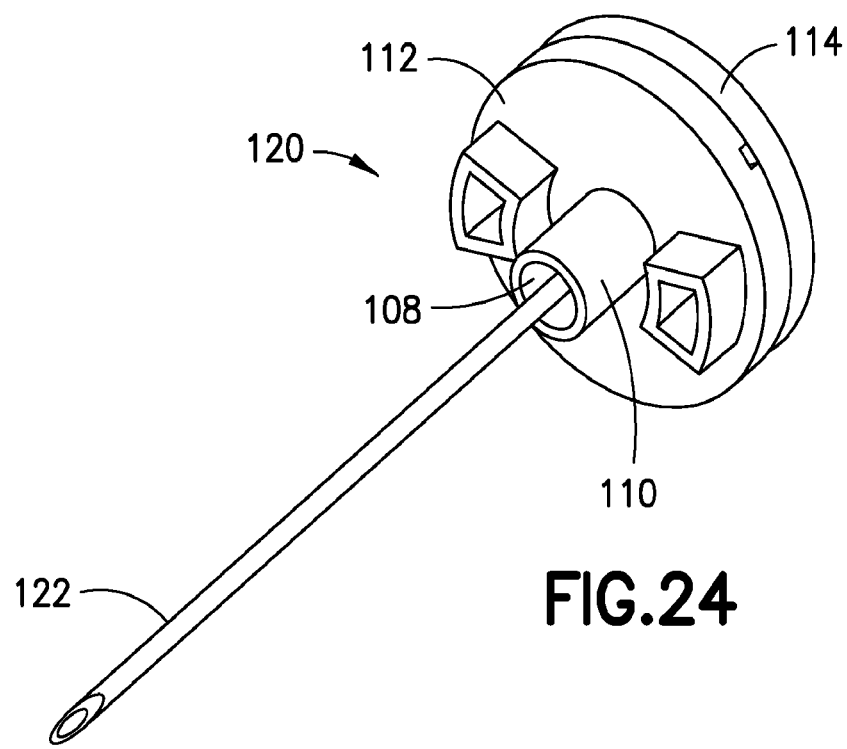
FIG. 24 is a perspective view of a third embodiment of pen needle according to the invention.
Figure 25:
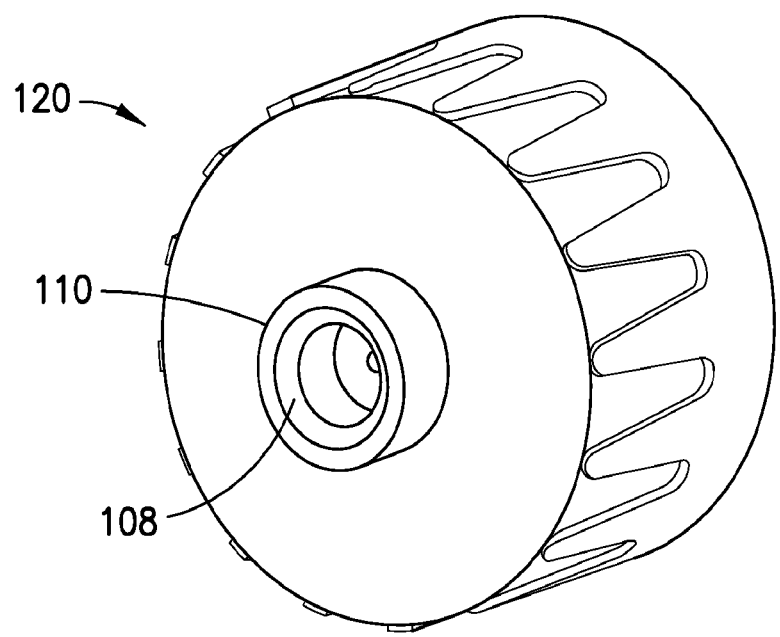
FIG. 25 is a perspective view of an interface according to the invention for use with the pen needle of FIG. 24.
Figure 28:
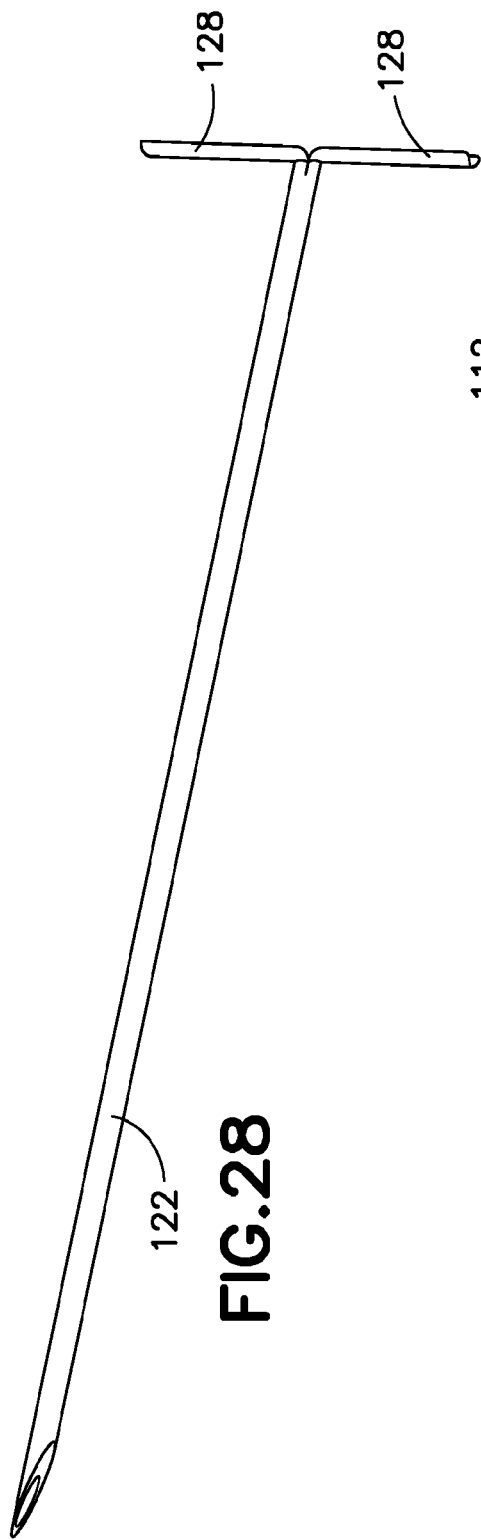
FIG. 28 is a perspective view of a cannula (needle) that is part of the pen needle of FIG. 24.
Figure 30:
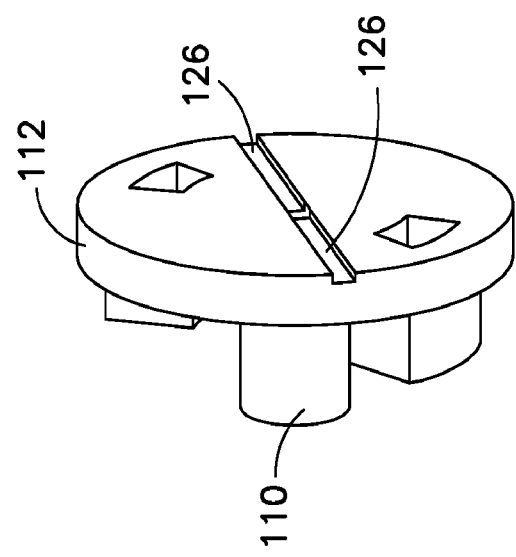
FIG. 30 is a rear perspective view thereof.
Figure 29:
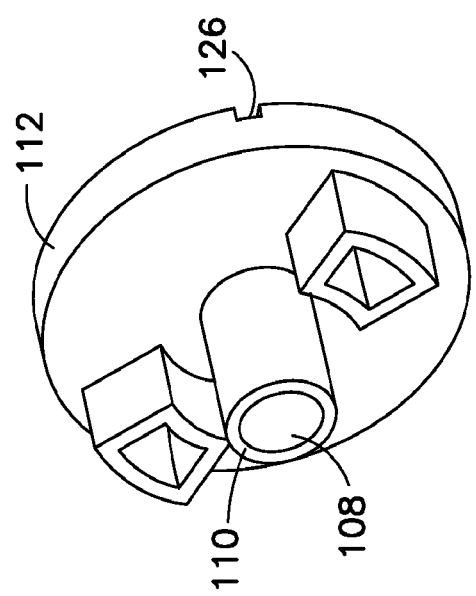
FIG. 29 is a front perspective view of the front (distal) hub portion of the pen needle of FIG. 24.
Figure 31:
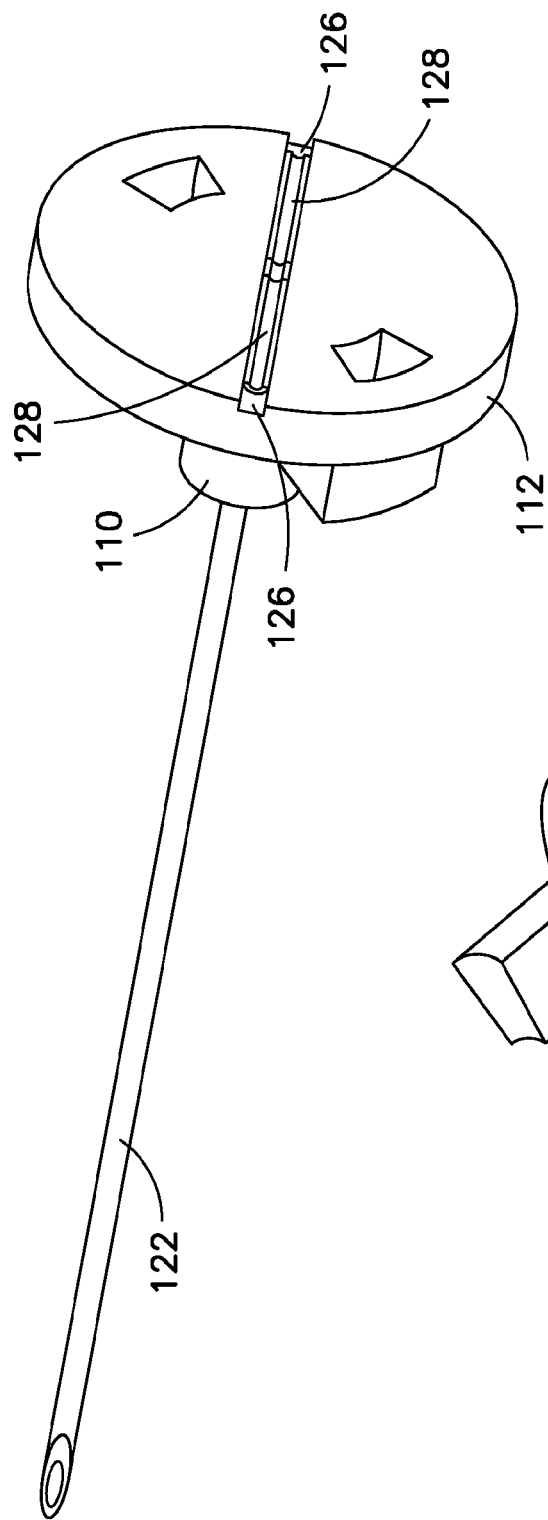
FIG. 31 is a rear perspective view of the cannula of FIG. 28 assembled with the front (distal) hub portion of FIG. 30.
Figure 32:
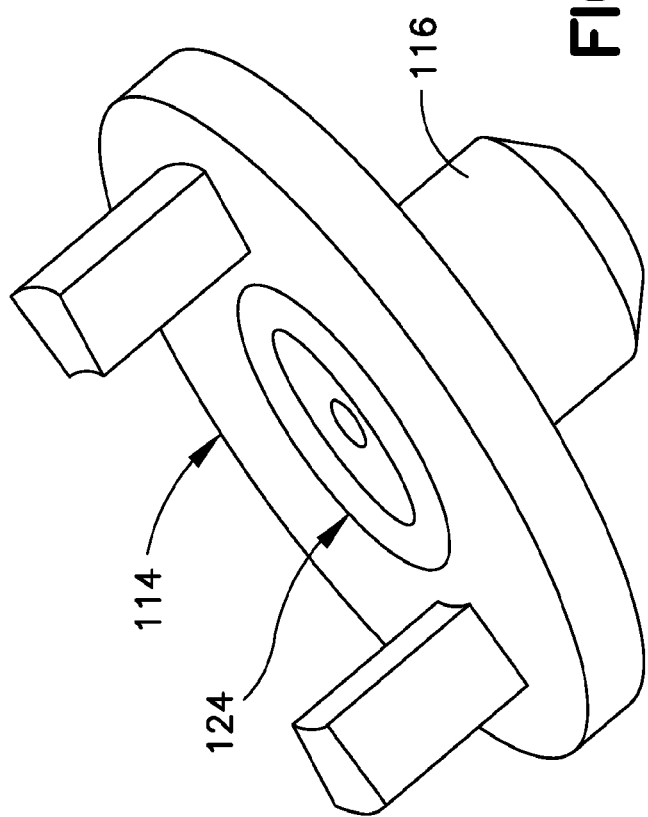
FIG. 32 is a front perspective view of the rear (proximal) hub portion of the pen needle of FIG. 24.
Figure 33:
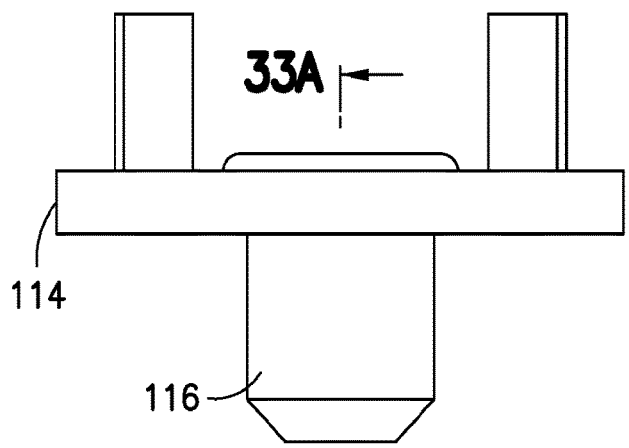
FIG. 33 is a front elevational view thereof.
Figure 33A:
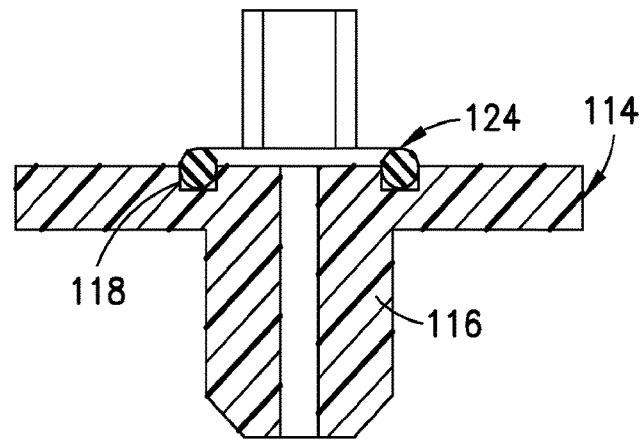
FIG. 33A is a cross-sectional view thereof taken along line 33A-33A in FIG. 33.
Figure 34:
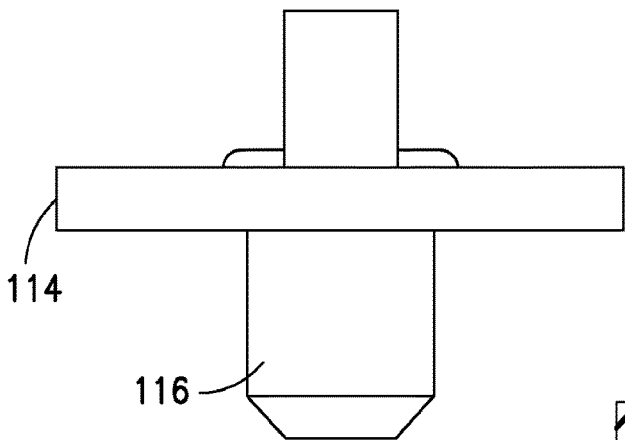
FIG. 34 is a side elevational view thereof.
Figure 34A:
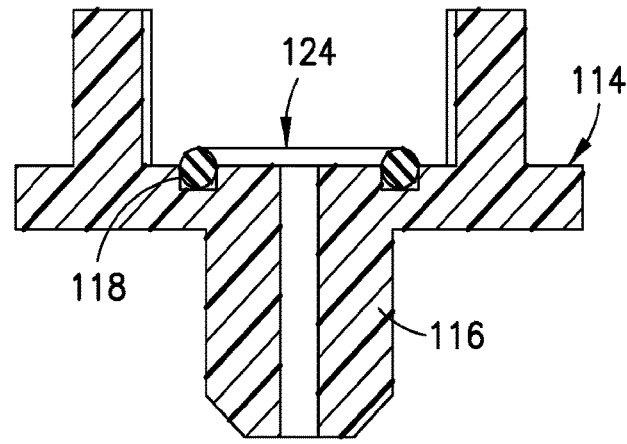
FIG. 34A is a cross-sectional view thereof taken along line 34A-34A in FIG. 34.
Figure 35:
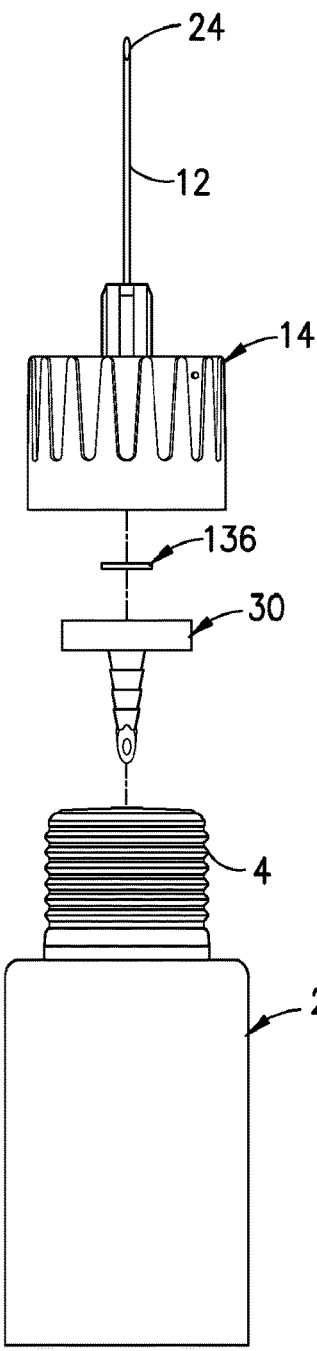
FIG. 35 is an exploded elevational view of a fourth embodiment of pen needle and mating interface according to the invention adjacent a conventional medication pen to which they can be attached.
Figure 36:
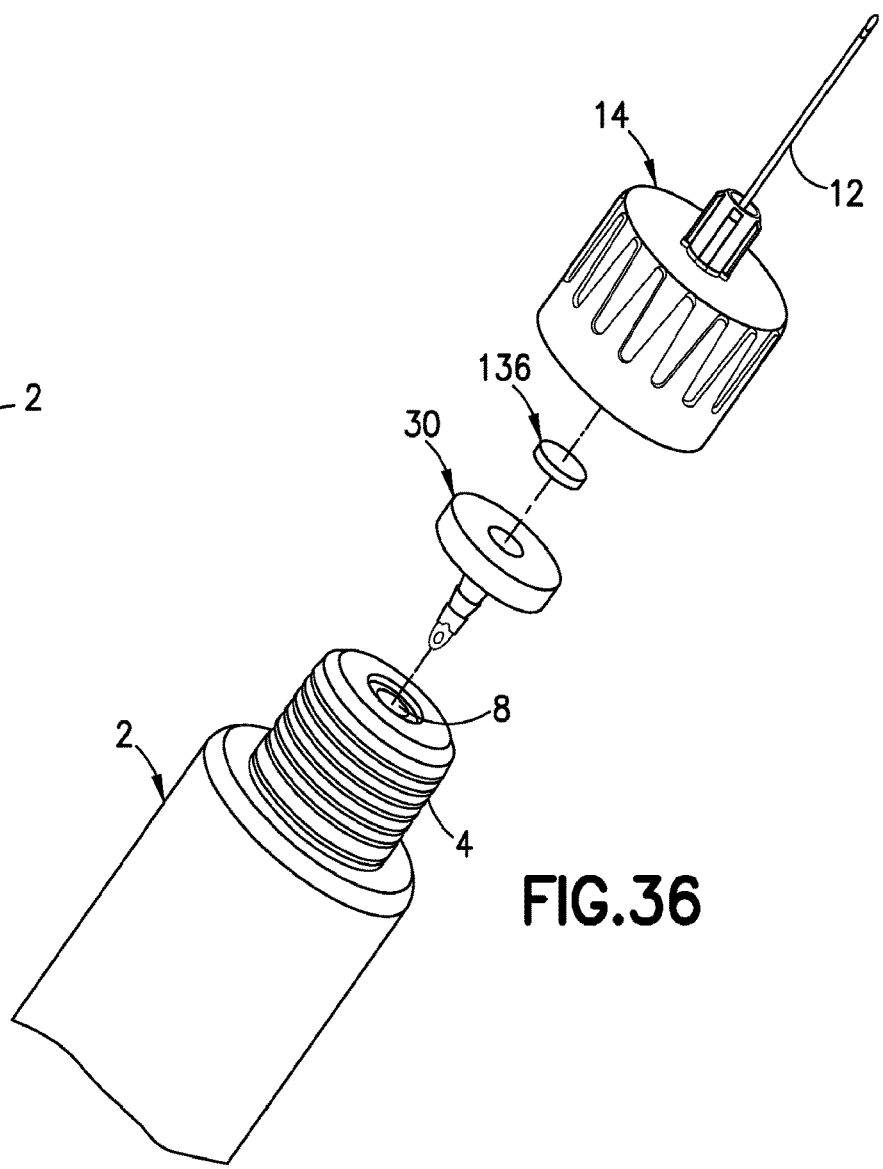
FIG. 36 is an exploded perspective view of the components shown in FIG. 33.
Figure 37:
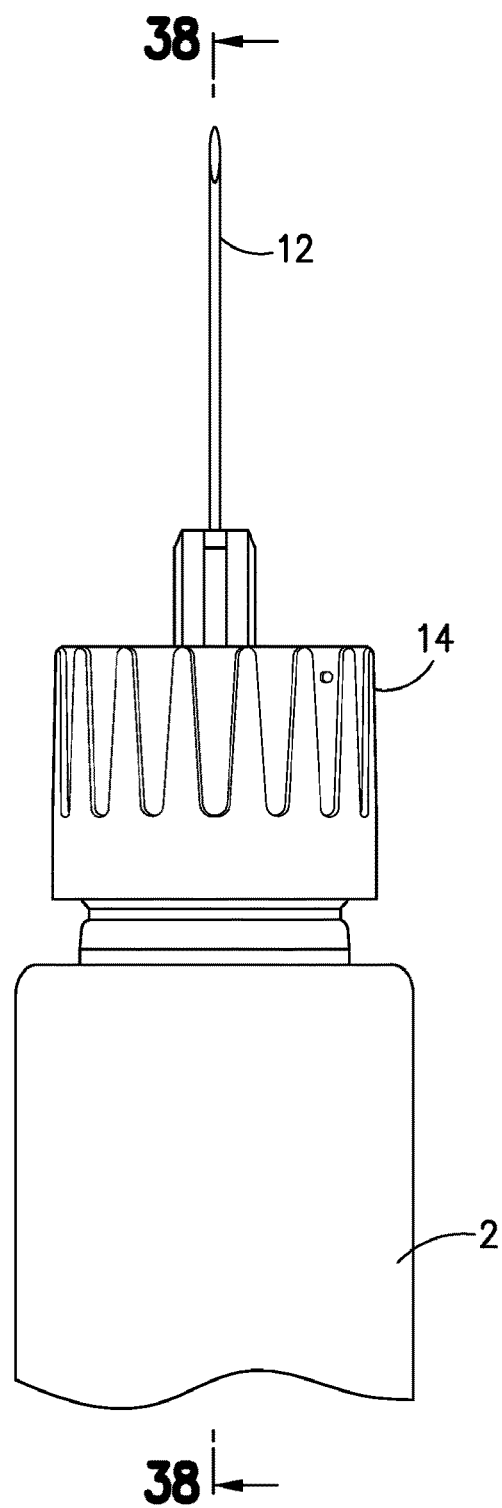
FIG. 37 is an elevational view of the assembled components shown in FIGS. 35 and 36.
Figure 38:
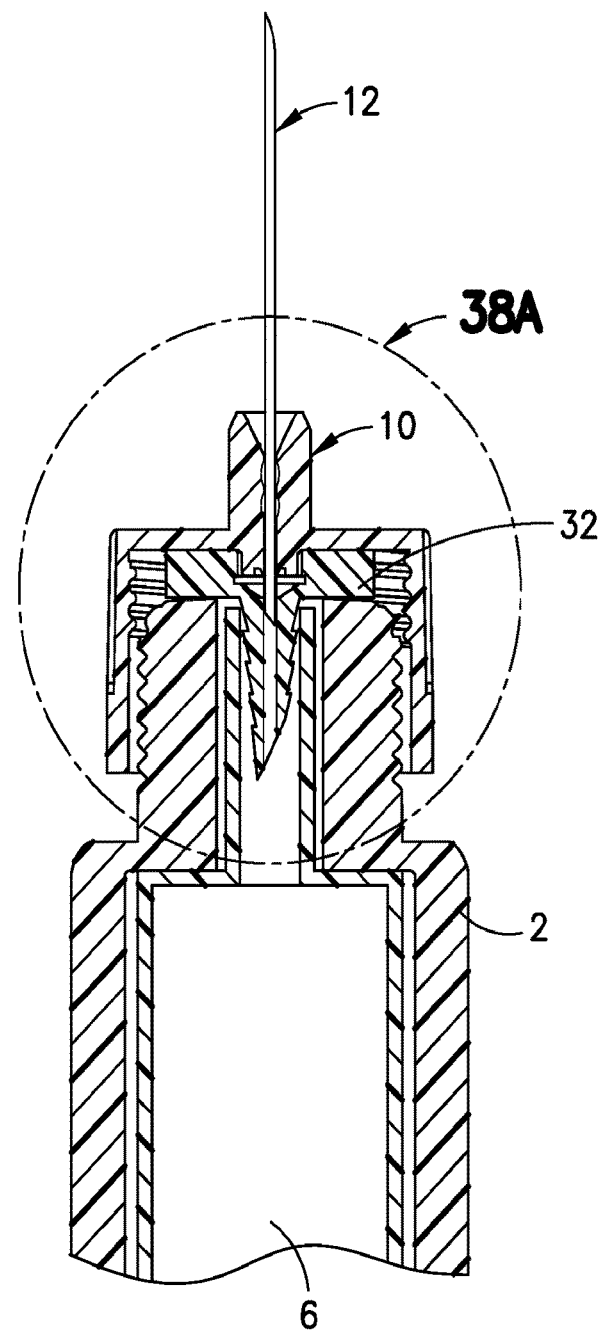
FIG. 38 is a cross-sectional view thereof taken along line 38-38 in FIG. 35.
Figure 38A:
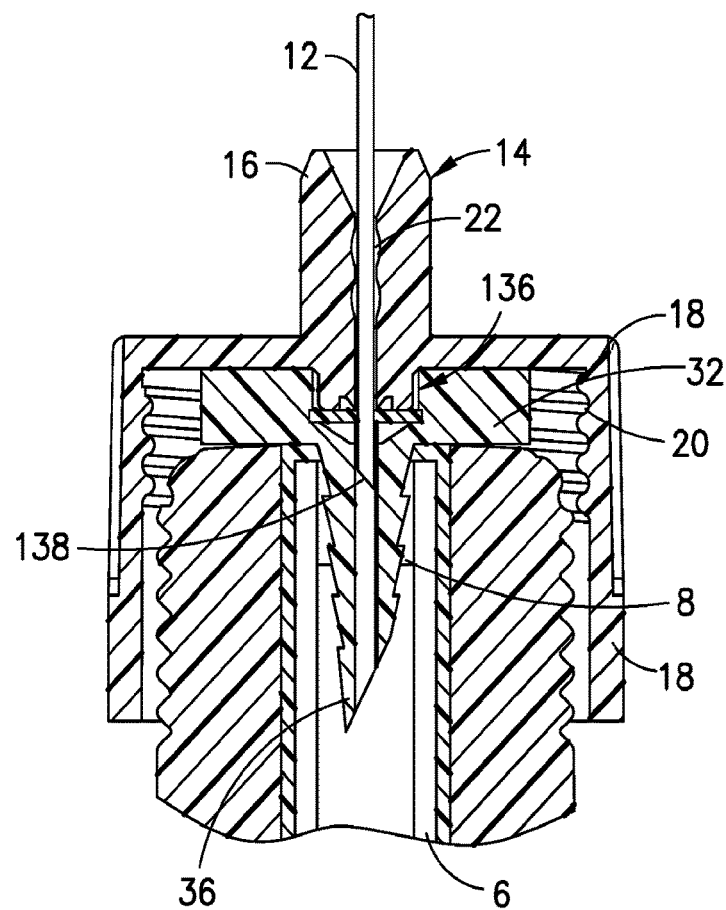
FIG. 38A is an enlarged, detail view thereof taken along line 38A-38A in FIG. 38.
Figure 39:
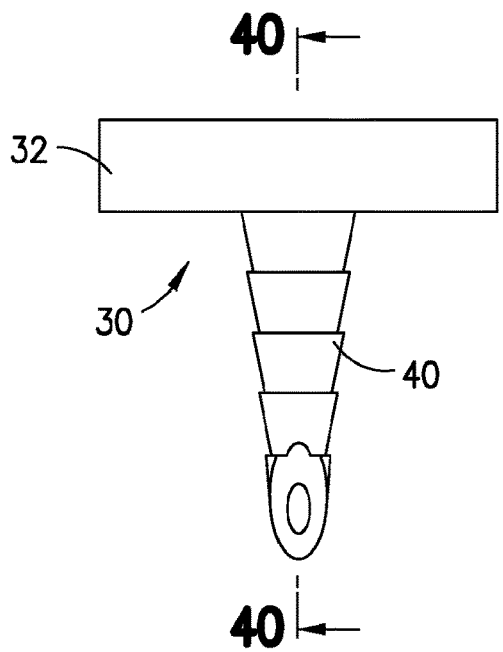
FIG. 39 is a front elevational view of the interface shown in FIG. 35.

Referring to FIGS. 14, 16, 17, 20 and 21, a second embodiment of medicament delivery system according to the invention includes a disposable pen needle 60 and a reusable interface member 80. Pen needle 60 has a hollow stainless steel needle (cannula) 62 fixed to a plastic hub 64. As seen in FIG. 17, hub 64 has a distal hub portion 66, an externally threaded proximal hub portion 68, and an axially extending hub bore 72 open at both ends. Needle 62 has a beveled and sharpened distal injection end 74 and a proximal needle portion 76 with a non-injection end 78. Proximal needle portion is fixed in hub bore 72 by any of the means previously described in regard to the first embodiment.

In this embodiment, too, the non-injection end 78 of the needle is not beveled or sharpened, and is not exposed outside of hub bore 72, so it cannot pierce the septum 8 of container 6. Septum piercing is accomplished instead by interface member 80, which has a proximally extending smooth spike 82 with an axial bore 84 open at both ends. Spike 82 is part of a molded body that includes an internally threaded collar 86 adapted to mate with the externally threaded end 4 of a medication pen 2. The body also includes a distally facing threaded recess 88 adapted to mate with the threaded proximal hub portion 68 of hub 64. The spike's axial bore 84 opens into recess 88. Thus, when interface member 80 is screwed onto medication pen 2, its spike 82 pierces septum 8 of container 6 and remains in place by virtue the threaded connection (see FIG. 21).

Capping of recess 88 prevents the escape of medicament from container 6 when no pen needle is installed. FIGS. 15, 17, 19, 20 and 21 show one type of capping solution: a press-on cap 90 similar to plug-type cap 46 of the previous embodiment, but preferably tethered to the body of interface member 80 to prevent misplacement of the cap. Cap 90, tether 92 and the body of interface member 80 preferably are integrally molded. Alternatively, cap 90 and tether 92 could be integrally formed and then attached to the body of member 80 by any suitable means; or all three could be separately formed and then joined. Other types of caps could also be used, such as an externally threaded plug, preferably tethered to the body of member 80.

Referring to FIGS. 24-27, a third embodiment of medicament delivery system according to the invention includes a reusable interface 100 and a disposable pen needle 120. Interface 100 is similar to interface 80 of the previous embodiment in that it has an internally threaded collar 102 adapted to mate with the externally threaded end 4 of a medication pen 2, and the collar surrounds a proximally extending smooth spike 104 having an open-ended axial bore 106. This embodiment also has a distally facing recess for mounting a pen needle, but the recess 108 in this embodiment is smooth and is formed in a distally projecting boss 110. In the absence of an installed pen needle, a plug-type cap would be needed to prevent leakage of medicament through recess 108. A properly configured plug-type cap, such as any of those described herein, would suffice for this purpose.

Referring to FIGS. 28-34A, pen needle 120 is an assembly comprising a hollow cannula (needle) 122 that is beveled and sharpened at its distal injection end. The proximal portion of the needle 112 is held between a distal hub portion 112 and a proximal hub portion 114. Boss 110, through which cannula 122 extends, is formed on distal hub portion 112. A proximally projecting mounting boss 116 is formed on proximal hub portion 114 and is configured to mate with recess 108 of interface 100 to form a tight fitting (e.g., a Luer taper fitting). Proximal hub portion 114 also has an annular groove 118 that accommodates an annular seal (O-ring) 124 that prevents medicament seepage from between the two hub portions.

The rear mating (inner) face of distal hub portion 112 has at least two grooves 126 that radiate from the central hub bore. Grooves 126 accommodate respective split ends 128 of the stainless steel cannula 122, which are formed by a laser or other suitable means. Distal hub portion 112 also has two recesses or windows 132 configured to receive and preferably tightly mate with two distally facing lugs 130 on proximal hub portion 114. After the cannula 122 is mounted in the hub bore segment of distal hub portion 112 with its split ends in grooves 126, the two hub portions 112, 114 are pressed together with their hub bore segments aligned. The two hub portions are held together by frictional and/or tight mechanical locking engagement of lugs 130 in recesses 132, which eliminates the need for applying adhesive or undergoing a curing process. Thus, in this embodiment too, the non-injection end 128 of the needle 122 is not beveled, sharpened or exposed outside of the hub bore.

The embodiment shown in FIGS. 35-40 is similar to the first embodiment, except that part of the proximal portion of the needle (cannula) is exposed; however, the exposed part is quite short and the non-injection end of the needle is well shielded. For the sake of brevity and convenience, in these figures like parts are designated by the same reference numbers used in the description of the first embodiment (FIGS. 1-8C), and the description will focus on the differences.

Figure 40:
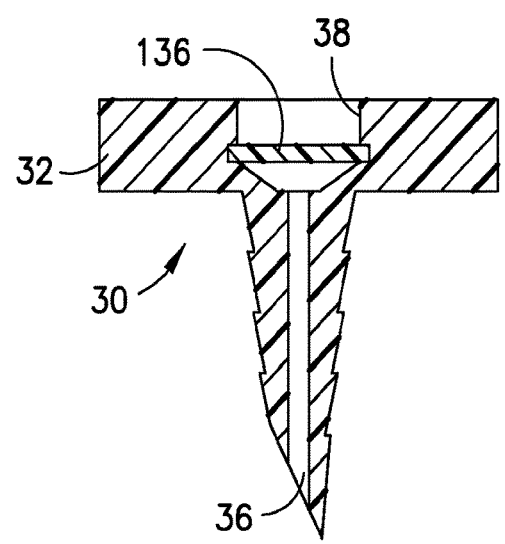
FIG. 40 is a cross-sectional view thereof taken along line 40-40 in FIG. 39.

Referring to FIG. 40, a relatively relatively thin septum 136 is fixed in recess 38 to form a seal that prevents leakage of medicament through axial bore 36 and recess 38 when no pen needle is installed. Septum 136 is made of any conventional material known in the art that is self-sealing if punctured by a sufficiently thin cannula, such as needle 12. Thus, the non-injection end 138 of needle 12 is beveled and sharpened, and projects beyond hub bore 22 just enough to pierce septum 136 when the pen needle is fully installed. Preferably, needle 12 projects far enough to enter spike bore 36, although that is not essential. In order to maintain adequate rigidity of the proximal end of needle 12 and still prevent needle stick injuries, the projecting distance of its non-injection end 138 from the hub 14 preferably should be no longer than necessary to accomplish the task of piercing septum 136: preferably no more than about one-half the length of the hub bore; more preferably no more than about one-third the length of the hub bore; and most preferably no more than about one-fourth the length of the hub bore. Even a projection of one-half the length of the hub bore would leave the non-injection end 138 well protected by the surrounding collar 18.

In each of the above-described embodiments, the flow of medicament to the stainless steel needle is enhanced due to the larger lumen of the plastic interface that directly feeds medicament to the needle. This allows the use of even smaller gauge needles for improved patient comfort. The abbreviated (concealed or very short) non-patient end of the needle also minimizes the risk of needle stick injuries.

The above description of preferred embodiments is not to be deemed limiting of the invention, which is defined by the following claims and their equivalents.

The invention claimed is:

1. A disposable pen needle, comprising:
a hub having a distal hub portion, a proximal hub portion adapted for attachment to a medicament delivery device, and a hub bore extending through the hub from the distal hub portion to the proximal hub portion, and
a needle mounted to the hub, the needle having a distal injection end and a proximal needle portion that is not exposed, the proximal needle portion terminating in a non-injection end,
wherein at least part of the proximal needle portion resides in the hub bore, and
wherein the distal hub portion and the proximal hub portion are separately formed parts, each having a respective hub bore segment, the hub portions being joined together with their hub bore segments aligned; and
wherein the non-injection end of the needle is split into a plurality of legs that are turned outward and sandwiched between the distal hub portion and the proximal hub portion.

2. The disposable pen needle of claim 1, wherein the proximal hub portion includes a mounting boss through which the hub bore extends.

3. The disposable pen needle of claim 1, including an annular seal between the distal hub portion and the proximal hub portion and positioned to prevent medicament leakage from the bore segments.

4. The disposable pen needle of claim 1, wherein each leg of the needle is accommodated in a notch in at least one of the hub portions.

5. The disposable pen needle of claim 4, wherein the notches are in the distal hub portion.

6. The disposable pen needle of claim 1, wherein one of the hub portions has at least one lug facing the other hub portion, and the other hub portion has at least one recess, each recess accommodating a respective lug.

7. The disposable pen needle of claim 6, wherein the at least one lug is on the proximal hub portion, and the at least one recess is in the distal hub portion.

8. The disposable pen needle of claim 1, wherein the non-injection end of the needle is neither beveled nor sharpened.

9. The disposable pen needle of claim 1, wherein the thickness of the injection end of the needle is smaller than 32 gauge.

10. A combination comprising:
the disposable pen needle according to claim 1,
a reusable interface adapted for use between a medicament delivery device and the disposable pen needle, comprising:
a body having a spike adapted to pierce a seal of a medicament container housed in the device, and a recess axially aligned with the spike and adapted to mate with the disposable pen needle, the body having an annular groove in a distal face thereof; and
an annular seal seated in the annular groove to enhance sealing with a hub of the disposable pen needle;
wherein the spike has an axial bore that extends through the spike and communicates with the recess.

11. The combination according to claim 10, wherein:
the proximal hub portion of the disposable pen needle includes a proximally projecting mounting boss; and
the body of the reusable interface includes a recess configured to mate with the mounting boss of the disposable pen needle.

* * * * *